US008273527B2

(12) United States Patent
Bartholomeusz et al.

(10) Patent No.: US 8,273,527 B2
(45) Date of Patent: *Sep. 25, 2012

(54) VIRAL VARIANTS

(75) Inventors: Angeline Bartholomeusz, Carnegie (AU); Margaret Littlejohn, Coburg (AU); Anna Ayres, West Brunswick (AU); Stephen Locarnini, East St Kilda (AU)

(73) Assignee: Melbourne Health, Parkville (AU)

( * ) Notice: Subject to any disclaimer, the term of this patent is extended or adjusted under 35 U.S.C. 154(b) by 702 days.

This patent is subject to a terminal disclaimer.

(21) Appl. No.: 11/905,904

(22) Filed: Oct. 5, 2007

(65) Prior Publication Data

US 2008/0171313 A1 Jul. 17, 2008

Related U.S. Application Data

(63) Continuation of application No. 09/958,503, filed as application No. PCT/AU00/00294 on Apr. 7, 2000, now Pat. No. 7,291,453.

(30) Foreign Application Priority Data

Apr. 9, 1999 (AU) .......................................... 9679

(51) Int. Cl.
*C12Q 1/70* (2006.01)
*C12Q 1/68* (2006.01)

(52) U.S. Cl. .......................................... 435/5; 435/6.1

(58) Field of Classification Search ........................ None
See application file for complete search history.

(56) References Cited

U.S. PATENT DOCUMENTS 7,291,453 B1 * 11/2007 Bartholomeusz et al. ........ 435/5

FOREIGN PATENT DOCUMENTS

| | | |
|---|---|---|
| WO | WO 91/14703 | 10/1991 |
| WO | WO 94/21812 | 9/1994 |
| WO | WO 94/26904 | 11/1994 |
| WO | WO 98/21317 | * 5/1998 |
| WO | WO 99/66047 | 12/1999 |
| WO | WO 00/28009 | 5/2000 |

OTHER PUBLICATIONS

Hussain et al., Journal of Viral Hepatitis 1999, vol. 6, pp. 183-194.*
Hannoun et al, "Long-term mutation rates in the hepatitis B virus genome", Journal of General Virology (2000), 81, 75-83.
Gunther et al, "Absence of mutations in the YMDD motif/B region of the hepatitis B virus polymerase in famciclovir therapy failure", Journal of Hepatology 1999; 30:749-754.
Angus, T. et al (Feb. 1993) "Combination antiviral therapy controls severe post-liver transplant recurrence of hepatitis B virus infection" J. Gastroenterol Hepatol 8:353:357.
Aye, T. et al (1997) "Hepatitis B virus polymerase mutations during antiviral therapy in a patient following liver transplantation" Journal of Hepatology 26:1148-1153.
Bartholomeusz et al (1997) "Clinical Experience with Famciclovir against Hepatitis B Virus" Intervirology 40:337-342.
Cariani, E. et al (1995) "Emergence of Hepatitis B Virus S Gene Mutant in a Liver Transplant Recipient" Journal of Medical Virology 47:410-415.
Carman, W. F. and Thomas H. C. (1992) "Genetic Viration in Hepatitis B Virus" Gastroenterology 102:711-719.
Ghany, M. G. et al (Jan. 1998) "Hepatitis B Virus S Mutants in Liver Transplant recipients Who Were Reinfected Despite Hepatitis B Immune Globulin Prophylaxis" Hepatology 27:213-222.
Main, J. et al. (1996) "A double blind, placebo-controlled study to assess the effect of famciclovir on virus replication in patients with chronic hepatitis B virus infection" J. Viral Hepatitis 3:211-215.
Moriyama, K. et al (Jan. 1991) "immunoselected hepatitis B virus mutant" Lancet 337:125.
Norder, H. et al (1993) "Genetic relatedness of hepatitis B viral strains of diverse geographical origin and natural variations in the primary structure of the surface antigen" J. Gen Virol 74:1341-1348.
Poch, O. et al (1989) "Identification of four conserved motifs among the RNA-dependent polymerase encoding elements" EMBO J. 8(12):3867-3874.
Protzer-Knolle, U. et al (1998) "Hepatitis B Virus with Antigenically Altered Hepatitis B Surface Antigen is Selected by High-Dose Hepatitis B Immune Globulin After Liver Transplantation" Hepatology 27:254-263.
Shaw, T. et al (Apr. 1994) "In Vitro Antiviral Activity of Penciclovir, a Novel Purine Nucleoside, against Duck Hepatitis B Virus" Antimicrobial Agents Chemotherapy 38(4):719-723.
Wallace, L. A. and Carman, W. F. (1997) "Surface Gene Variation of HBV: Scientific and Medical Relevance" Viral Hepatitis Reviews 3(1):5-16.
Oon et al, Antivira Research Apr. 1999, vol. 41, pp. 113-118.
Terrault et al, Hepatology Aug. 1998, vol. 28, No. 2, pp. 555-561.
Ling et al, Journal of General Virology 1990, vol. 80, pp. 601-606.
Tipples et al, Hepatology 1996, vol. 24, No. 3, pp. 714-717.
Bartholomew et al, The Lancet 1997, vol. 349, No. 9044, pp. 20-22.
Niesters et al, The Journal of Infectious Diseases 1998, vol. 177, pp. 1382-1385.
Pichoud et al, Hepatology Jan. 1999, vol. 29, No. 1, pp. 230-237.
Scaglioni et al, Virology 1997, vol. 233, pp. 374-381.
Moriyama et al, Fukuoka Igaku Zasshi 1994, vol. 85, pp. 314-322.
Bartholomeusz et al, Intervirology 1997, vol. 40, No. 5-6, pp. 337-342.
Carman et al, Hepatology Sep. 1996, vol. 24, No. 3, pp. 489-493.
de Man et al, Journal of Hepatology 1998, vol. 29, No. 4, pp. 669-675.
Torresi et al, Journal of Hepatology, 1999, vol. 30, No. Suppl. 1, p. 62.

(Continued)

*Primary Examiner* — Mary E Mosher
*Assistant Examiner* — Myron Hill
(74) *Attorney, Agent, or Firm* — Nixon & Vanderhye P.C.

(57) ABSTRACT

The present invention relates generally to viral variants exhibiting reduced sensitivity to particular agents and/or reduced interactivity with immunological reagents. More particularly, the present invention is directed to hepatitis B virus variants exhibiting complete or partial resistance to nucleoside analogues and/or reduced interactivity with antibodies to viral surface components including reduced sensitivity. The present invention further contemplates assays for detecting such viral variants which assays are useful in monitoring anti-viral therapeutic regimes and in developing new or modified vaccines directed against viral agents and in particular hepatitis B virus variants.

1 Claim, 2 Drawing Sheets

OTHER PUBLICATIONS

Locarnini et al, Hepatology, 1999, vol. 30, No. Suppl. 1, p. 62.
International Search Report issued in connection with PCT/AU00/00294.
Supplementary Partial European Search Report issued in connection with EP 00 91 5035.
Tillmann et al, "Mutational Pattern of Hepatitis B Virus on Sequential Therapy With Famciclovir and Lamivudine in Patients With Hepatitis B Virus Reinfection Occurring Under HBIg Immunoglobulin After Liver Transplantation", Hepatology 1999; 30:244-256.
Seignères et al, "Evolution of Hepatitis B Virus Polymerase Gene Sequence during Famciclovir Therapy for Chronic Hepatitis B", The Journal of Infectious Diseases 2000; 181:1221-33.
Hussain et al, "Mutations in the hepatitis B virus polymerase gene associated with antiviral treatment for hepatitis B", Journal of Viral Hepatitis (1999), vol. 6, pp. 183-194.
Oon et al, "Hepatitis B virus variants with lamivudine-related mutations in the DNA polymerase and the 'a' epitope of the surface antigen are sensitive to ganciclovir", Antiviral Research Apr. 1999, vol. 41, pp. 113-118.
Terrault et al, "Incidence and Clinical Consequences of Surface and Polymerase Gene Mutations in Liver Transplant Recipients on Hepatitis B Immunoglobulin", Hepatology Aug. 1998, vol. 28, No. 2, pp. 555-561.
Ling et al, "Functional analysis of mutations conferring lamivudine resistance on hepatitis B virus", Journal of General Virology 1990, vol. 80, pp. 601-606.
Tipples et al, "Mutation in HBV RNA-Dependent DNA Polymerase Confer Resistance to Lamivudine In Vivo" Hepatology 1996, vol. 24, No. 3, pp. 714-717.
Bartholomew et al, "Hepatitis-B-virus resistance to lamivudine given for recurrent infection after orthotopic liver transplantation", The Lancet 1997, vol. 349, No. 9044, pp. 20-22.
Niesters et al, "Identification of More than One Mutation in the Hepatitis B Virus Polymerase Gene Arising during Prolonged Lamivudine Treatment", The Journal of Infectious Diseases 1998, vol. 177, pp. 1382-1385.
Pichoud et al, "Transient Selection of a Hepatitis B Virus Polymerase Gene Mutant Associated With a Decreased Replication Capacity and Famciclovir Resistance", Hepatology Jan. 1999, vol. 29, No. 1, pp. 230-237.
Scaglioni et al, "Biologic Properties of Hepatitis B Viral Genomes with Mutations in the Precore Promoter and Precore Open Reading Frame", Virology 1997, vol. 233, pp. 374-381.
Moriyama et al, "Mutations in the transcriptional regulatory region of the precore and core/pregenome of a hepatitis B virus with defective HBeAg production", Fukuoka Igaku Zasshi 1994, vol. 85, pp. 314-322.
Bartholomeusz et al, "Clinical Experience with Famciclovir against Hepatitis B Virus", Intervirology 1997, vol. 40, No. 5-6, pp. 337-342.
Carman et al, "Hepatitis B Virus Envelope Variation After Transplantation With and Without Hepatitis B Immune Globulin Prophylaxis", Hepatology Sep. 1996, vol. 24, No. 3, pp. 489-493.
de Man et al, "The sequential occurrence of viral mutations in a liver transplant recipient re-infected with hepatitis B: hepatitis B immune globulin escape, famciclovir non-response, followed by lamivudine resistance resulting in graft loss", Journal of Hepatology 1998, vol. 29, No. 4, pp. 669-675.
Torresi et al, "Significance of Envelope Protein Variants of Hepatitis B Virus Selected by Treatment with Antiviral Nucleoside Analogues", Journal of Hepatology, 1999, vol. 30, No. Suppl. 1, p. 62.
Locarnini et al, "Analysis of Hepatitis B Virus Polymerase Mutations in Orthotopic Liver Transplant Patients Receiving Famciclovir and HBIG", Hepatology, 1999, vol. 30, No. Suppl. 1, p. 62.

* cited by examiner

DOMAIN A 421 430 440 450

S$^{N}_{D}$LSWLSLD VSAAFYH$^{I}_{P}$PL HPAAMPHLL$^{I}_{V}$ GSSGL$^{S}_{D}$RYVA 460 470 480 490

RLSS$^{T}_{N}$S$^{R}_{N}$$^{N}_{I}$*N $^{N}$Y$_{H}$Q$^{H}_{Y}$$^{G}_{R}$***$^{D}_{N}$LH $^{D}_{N}$$^{S}_{Y}$CSR$^{N}_{Q}$LYVS L$^{L}_{M}$LLY$^{K}_{Q}$T$^{Y}_{F}$G$^{R}_{W}$

DOMAIN B 500 510 520 530

KLHL$^{Y}$L$^{S}_{A}$HPI$^{I}_{V}$ LGFRK$^{I}$LPMG$^{V}_{G}$ GLSPFLLAQF TSAI$^{C}_{L}$$^{A}_{S}$$^{V}_{M}$$^{V}_{T}$$^{R}$CR

DOMAIN C 540 550 560

AF$^{F}$PHC$^{L}_{V}$$^{A}_{V}$F$^{S}_{A}$Y MDD$^{V}$L$_{M}$VLGA$^{K}_{R}$$^{S}_{T}$ $^{V}_{G}$Q$_{E}$H$^{L}$S$_{R}$E$^{S}_{F}$L$^{F}_{Y}$$^{T}_{A}$$^{A}_{S}$

DOMAIN D DOMAIN E 570 580 590 600

$^{V}_{I}$$^{T}_{C}$$^{N}_{S}$$^{F}$VLL$^{S}_{D}$$^{L}$VGI HLNP$^{N}_{Q}$KTKRW GYSLNFMGY$^{V}_{I}$I G

Figure 2

SEQUENCE LISTING

<160> NUMBER OF SEQ ID NOS: 10

<210> SEQ ID NO 1
<211> LENGTH: 23
<212> TYPE: DNA
<213> ORGANISM: Hepatitis B virus

<400> SEQUENCE: 1
gcctcatttt gtgggtcacc ata 23

<210> SEQ ID NO 2
<211> LENGTH: 20
<212> TYPE: DNA
<213> ORGANISM: Hepatitis B virus

<400> SEQUENCE: 2
tctctgacat actttccaat 20

<210> SEQ ID NO 3
<211> LENGTH: 21
<212> TYPE: DNA
<213> ORGANISM: Hepatitis B virus

<400> SEQUENCE: 3
ttggggtgga gccctcaggt c 21

<210> SEQ ID NO 4
<211> LENGTH: 18
<212> TYPE: DNA
<213> ORGANISM: Hepatitis B virus

<400> SEQUENCE: 4
aaattcgcag tccccaac 18

<210> SEQ ID NO 5
<211> LENGTH: 18
<212> TYPE: DNA
<213> ORGANISM: Hepatitis B virus

<400> SEQUENCE: 5
gaaaattggt aacagcgg 18

<210> SEQ ID NO 6
<211> LENGTH: 19
<212> TYPE: DNA
<213> ORGANISM: Hepatitis B virus

<400> SEQUENCE: 6
gtatccctcc tgttgctgt 19

<210> SEQ ID NO 7
<211> LENGTH: 181
<212> TYPE: PRT
<213> ORGANISM: Hepatitis B virus
<220> FEATURE:
<221> NAME/KEY: MISC_FEATURE
<222> LOCATION: (48)..(48)
<223> OTHER INFORMATION: Xaa is any amino acid
<220> FEATURE:
<221> NAME/KEY: MISC_FEATURE
<222> LOCATION: (2)..(2)
<223> OTHER INFORMATION: Xaa is Asn or Asp
<220> FEATURE:
<221> NAME/KEY: MISC_FEATURE
<222> LOCATION: (17)..(17)

<223> OTHER INFORMATION: Xaa is Ile or Pro
<220> FEATURE:
<221> NAME/KEY: MISC_FEATURE
<222> LOCATION: (29)..(29)
<223> OTHER INFORMATION: Xaa is Ile or Val
<220> FEATURE:
<221> NAME/KEY: MISC_FEATURE
<222> LOCATION: (35)..(35)
<223> OTHER INFORMATION: Xaa is Ser or Asp
<220> FEATURE:
<221> NAME/KEY: MISC_FEATURE
<222> LOCATION: (44)..(44)
<223> OTHER INFORMATION: Xaa is Thr or Asn
<220> FEATURE:
<221> NAME/KEY: MISC_FEATURE
<222> LOCATION: (46)..(46)
<223> OTHER INFORMATION: Xaa is  Arg or Asn
<220> FEATURE:
<221> NAME/KEY: MISC_FEATURE
<222> LOCATION: (47)..(47)
<223> OTHER INFORMATION: Xaa is Asn or Ile
<220> FEATURE:
<221> NAME/KEY: MISC_FEATURE
<222> LOCATION: (50)..(50)
<223> OTHER INFORMATION: Xaa is Asn or Tyr or His
<220> FEATURE:
<221> NAME/KEY: MISC_FEATURE
<222> LOCATION: (52)..(52)
<223> OTHER INFORMATION: Xaa is His or Tyr
<220> FEATURE:
<221> NAME/KEY: MISC_FEATURE
<222> LOCATION: (53)..(53)
<223> OTHER INFORMATION: Xaa is Gly or Arg
<220> FEATURE:
<221> NAME/KEY: MISC_FEATURE
<222> LOCATION: (54)..(56)
<223> OTHER INFORMATION: Xaa is any amino acid
<220> FEATURE:
<221> NAME/KEY: MISC_FEATURE
<222> LOCATION: (57)..(57)
<223> OTHER INFORMATION: Xaa is Asp or Asn
<220> FEATURE:
<221> NAME/KEY: MISC_FEATURE
<222> LOCATION: (60)..(60)
<223> OTHER INFORMATION: Xaa is Asp or Asn
<220> FEATURE:
<221> NAME/KEY: MISC_FEATURE
<222> LOCATION: (61)..(61)
<223> OTHER INFORMATION: Xaa is Ser or Tyr
<220> FEATURE:
<221> NAME/KEY: MISC_FEATURE
<222> LOCATION: (65)..(65)
<223> OTHER INFORMATION: Xaa is Asn or Gln
<220> FEATURE:
<221> NAME/KEY: MISC_FEATURE
<222> LOCATION: (71)..(71)
<223> OTHER INFORMATION: Xaa is Leu or Met
<220> FEATURE:
<221> NAME/KEY: MISC_FEATURE
<222> LOCATION: (75)..(75)
<223> OTHER INFORMATION: Xaa is Lys or Gln
<220> FEATURE:
<221> NAME/KEY: MISC_FEATURE
<222> LOCATION: (77)..(77)
<223> OTHER INFORMATION: Xaa is Tyr or Phe
<220> FEATURE:
<221> NAME/KEY: MISC_FEATURE
<222> LOCATION: (79)..(79)
<223> OTHER INFORMATION: Xaa is Arg or Trp
<220> FEATURE:
<221> NAME/KEY: MISC_FEATURE
<222> LOCATION: (84)..(84)
<223> OTHER INFORMATION: Xaa is Tyr or Leu
<220> FEATURE:
<221> NAME/KEY: MISC_FEATURE
<222> LOCATION: (85)..(85)
<223> OTHER INFORMATION: Xaa is Ser or Ala
<220> FEATURE:
<221> NAME/KEY: MISC_FEATURE
<222> LOCATION: (89)..(89)

<223> OTHER INFORMATION: Xaa is Ile or Val
<220> FEATURE:
<221> NAME/KEY: MISC_FEATURE
<222> LOCATION: (95)..(95)
<223> OTHER INFORMATION: Xaa is Ile or Leu
<220> FEATURE:
<221> NAME/KEY: MISC_FEATURE
<222> LOCATION: (99)..(99)
<223> OTHER INFORMATION: Xaa is Val or Gly
<220> FEATURE:
<221> NAME/KEY: MISC_FEATURE
<222> LOCATION: (114)..(114)
<223> OTHER INFORMATION: Xaa is Cys or Leu
<220> FEATURE:
<221> NAME/KEY: MISC_FEATURE
<222> LOCATION: (115)..(115)
<223> OTHER INFORMATION: Xaa is Ala or Ser
<220> FEATURE:
<221> NAME/KEY: MISC_FEATURE
<222> LOCATION: (116)..(116)
<223> OTHER INFORMATION: Xaa is Val or Met
<220> FEATURE:
<221> NAME/KEY: MISC_FEATURE
<222> LOCATION: (117)..(117)
<223> OTHER INFORMATION: Xaa is Val or Thr
<220> FEATURE:
<221> NAME/KEY: MISC_FEATURE
<222> LOCATION: (118)..(118)
<223> OTHER INFORMATION: Xaa is Arg or Cys
<220> FEATURE:
<221> NAME/KEY: MISC_FEATURE
<222> LOCATION: (122)..(122)
<223> OTHER INFORMATION: Xaa is Phe or Pro
<220> FEATURE:
<221> NAME/KEY: MISC_FEATURE
<222> LOCATION: (125)..(125)
<223> OTHER INFORMATION: Xaa is Leu or Val
<220> FEATURE:
<221> NAME/KEY: MISC_FEATURE
<222> LOCATION: (126)..(126)
<223> OTHER INFORMATION: Xaa is Ala or Val
<220> FEATURE:
<221> NAME/KEY: MISC_FEATURE
<222> LOCATION: (128)..(128)
<223> OTHER INFORMATION: Xaa is Ser or Ala
<220> FEATURE:
<221> NAME/KEY: MISC_FEATURE
<222> LOCATION: (133)..(133)
<223> OTHER INFORMATION: Xaa is Val or Leu or Met
<220> FEATURE:
<221> NAME/KEY: MISC_FEATURE
<222> LOCATION: (138)..(138)
<223> OTHER INFORMATION: Xaa is Lys or Arg
<220> FEATURE:
<221> NAME/KEY: MISC_FEATURE
<222> LOCATION: (139)..(139)
<223> OTHER INFORMATION: Xaa is Ser or Thr
<220> FEATURE:
<221> NAME/KEY: MISC_FEATURE
<222> LOCATION: (140)..(140)
<223> OTHER INFORMATION: Xaa is Val or Gly
<220> FEATURE:
<221> NAME/KEY: MISC_FEATURE
<222> LOCATION: (141)..(141)
<223> OTHER INFORMATION: Xaa is Gln or Glu
<220> FEATURE:
<221> NAME/KEY: MISC_FEATURE
<222> LOCATION: (143)..(143)
<223> OTHER INFORMATION: Xaa is Leu or Ser or Arg
<220> FEATURE:
<221> NAME/KEY: MISC_FEATURE
<222> LOCATION: (145)..(145)
<223> OTHER INFORMATION: Xaa is Ser or Phe
<220> FEATURE:
<221> NAME/KEY: MISC_FEATURE
<222> LOCATION: (147)..(147)
<223> OTHER INFORMATION: Xaa is Phe or Tyr
<220> FEATURE:
<221> NAME/KEY: MISC_FEATURE
<222> LOCATION: (148)..(148)

<223> OTHER INFORMATION: Xaa is Thr or Ala
<220> FEATURE:
<221> NAME/KEY: MISC_FEATURE
<222> LOCATION: (149)..(149)
<223> OTHER INFORMATION: Xaa is Ala or Ser
<220> FEATURE:
<221> NAME/KEY: MISC_FEATURE
<222> LOCATION: (150)..(150)
<223> OTHER INFORMATION: Xaa is Val or Ile
<220> FEATURE:
<221> NAME/KEY: MISC_FEATURE
<222> LOCATION: (151)..(151)
<223> OTHER INFORMATION: Xaa is Thr or Cys
<220> FEATURE:
<221> NAME/KEY: MISC_FEATURE
<222> LOCATION: (152)..(152)
<223> OTHER INFORMATION: Xaa is Asn or Ser
<220> FEATURE:
<221> NAME/KEY: MISC_FEATURE
<222> LOCATION: (153)..(153)
<223> OTHER INFORMATION: Xaa is Phe or Val
<220> FEATURE:
<221> NAME/KEY: MISC_FEATURE
<222> LOCATION: (156)..(156)
<223> OTHER INFORMATION: Xaa is Ser or Asp
<220> FEATURE:
<221> NAME/KEY: MISC_FEATURE
<222> LOCATION: (157)..(157)
<223> OTHER INFORMATION: Xaa is Leu or Val
<220> FEATURE:
<221> NAME/KEY: MISC_FEATURE
<222> LOCATION: (164)..(164)
<223> OTHER INFORMATION: Xaa is Asn or Gln
<220> FEATURE:
<221> NAME/KEY: MISC_FEATURE
<222> LOCATION: (179)..(179)
<223> OTHER INFORMATION: Xaa is Val or Ile
<220> FEATURE:
<221> NAME/KEY: MISC_FEATURE
<222> LOCATION: (130)..(130)
<223> OTHER INFORMATION: M is amino acid 550

<400> SEQUENCE: 7

```
Ser Xaa Leu Ser Trp Leu Ser Leu Asp Val Ser Ala Ala Phe Tyr His
1               5                   10                  15

Xaa Pro Leu His Pro Ala Ala Met Pro His Leu Leu Xaa Gly Ser Ser
            20                  25                  30

Gly Leu Xaa Arg Tyr Val Ala Arg Leu Ser Ser Xaa Ser Xaa Xaa Xaa
        35                  40                  45

Asn Xaa Gln Xaa Xaa Xaa Xaa Xaa Xaa Leu His Xaa Xaa Cys Ser Arg
    50                  55                  60

Xaa Leu Tyr Val Ser Leu Xaa Leu Leu Tyr Xaa Thr Xaa Gly Xaa Lys
65                  70                  75                  80

Leu His Leu Xaa Xaa His Pro Ile Xaa Leu Gly Phe Arg Lys Xaa Pro
                85                  90                  95

Met Gly Xaa Gly Leu Ser Pro Phe Leu Leu Ala Gln Phe Thr Ser Ala
            100                 105                 110

Ile Xaa Xaa Xaa Xaa Xaa Arg Ala Phe Xaa His Cys Xaa Xaa Phe Xaa
        115                 120                 125

Tyr Met Asp Asp Xaa Val Leu Gly Ala Xaa Xaa Xaa Xaa His Xaa Glu
    130                 135                 140

Xaa Leu Xaa Xaa Xaa Xaa Xaa Xaa Xaa Leu Leu Xaa Xaa Gly Ile His
145                 150                 155                 160

Leu Asn Pro Xaa Lys Thr Lys Arg Trp Gly Tyr Ser Leu Asn Phe Met
                165                 170                 175

Gly Tyr Xaa Ile Gly
            180
```

<210> SEQ ID NO 8
<211> LENGTH: 181
<212> TYPE: PRT
<213> ORGANISM: Hepatitis B virus
<220> FEATURE:
<221> NAME/KEY: MISC_FEATURE
<222> LOCATION: (2)..(2)
<223> OTHER INFORMATION: Xaa is Asn or Asp
<220> FEATURE:
<221> NAME/KEY: MISC_FEATURE
<222> LOCATION: (17)..(17)
<223> OTHER INFORMATION: Xaa is Ile or Pro
<220> FEATURE:
<221> NAME/KEY: MISC_FEATURE
<222> LOCATION: (29)..(29)
<223> OTHER INFORMATION: Xaa is Ile or Val
<220> FEATURE:
<221> NAME/KEY: MISC_FEATURE
<222> LOCATION: (35)..(35)
<223> OTHER INFORMATION: Xaa is Ser or Asp
<220> FEATURE:
<221> NAME/KEY: MISC_FEATURE
<222> LOCATION: (44)..(44)
<223> OTHER INFORMATION: Xaa is Thr or Asn
<220> FEATURE:
<221> NAME/KEY: MISC_FEATURE
<222> LOCATION: (46)..(46)
<223> OTHER INFORMATION: Xaa is Arg or Asn
<220> FEATURE:
<221> NAME/KEY: MISC_FEATURE
<222> LOCATION: (47)..(47)
<223> OTHER INFORMATION: Xaa is Asn or Ile
<220> FEATURE:
<221> NAME/KEY: MISC_FEATURE
<222> LOCATION: (48)..(48)
<223> OTHER INFORMATION: Xaa is any amino acid
<220> FEATURE:
<221> NAME/KEY: MISC_FEATURE
<222> LOCATION: (50)..(50)
<223> OTHER INFORMATION: Xaa is Asn or Tyr or His
<220> FEATURE:
<221> NAME/KEY: MISC_FEATURE
<222> LOCATION: (52)..(52)
<223> OTHER INFORMATION: Xaa is His or Tyr
<220> FEATURE:
<221> NAME/KEY: MISC_FEATURE
<222> LOCATION: (53)..(53)
<223> OTHER INFORMATION: Xaa is Gly or Arg
<220> FEATURE:
<221> NAME/KEY: MISC_FEATURE
<222> LOCATION: (54)..(56)
<223> OTHER INFORMATION: Xaa is any amino acid
<220> FEATURE:
<221> NAME/KEY: MISC_FEATURE
<222> LOCATION: (57)..(57)
<223> OTHER INFORMATION: Xaa is Asp or Asn
<220> FEATURE:
<221> NAME/KEY: MISC_FEATURE
<222> LOCATION: (60)..(60)
<223> OTHER INFORMATION: Xaa is Asp or Asn
<220> FEATURE:
<221> NAME/KEY: MISC_FEATURE
<222> LOCATION: (61)..(61)
<223> OTHER INFORMATION: Xaa is Ser or Tyr
<220> FEATURE:
<221> NAME/KEY: MISC_FEATURE
<222> LOCATION: (65)..(65)
<223> OTHER INFORMATION: Xaa is Asn or Gln
<220> FEATURE:
<221> NAME/KEY: MISC_FEATURE
<222> LOCATION: (71)..(71)
<223> OTHER INFORMATION: Xaa is Leu or Met
<220> FEATURE:
<221> NAME/KEY: MISC_FEATURE
<222> LOCATION: (75)..(75)
<223> OTHER INFORMATION: Xaa is Lys or Gln
<220> FEATURE:
<221> NAME/KEY: MISC_FEATURE
<222> LOCATION: (77)..(77)

<223> OTHER INFORMATION: Xaa is Tyr or Phe
<220> FEATURE:
<221> NAME/KEY: MISC_FEATURE
<222> LOCATION: (79)..(79)
<223> OTHER INFORMATION: Xaa is Arg or Trp
<220> FEATURE:
<221> NAME/KEY: MISC_FEATURE
<222> LOCATION: (84)..(84)
<223> OTHER INFORMATION: Xaa is Tyr or Leu
<220> FEATURE:
<221> NAME/KEY: MISC_FEATURE
<222> LOCATION: (85)..(85)
<223> OTHER INFORMATION: Xaa is Ser or Ala
<220> FEATURE:
<221> NAME/KEY: MISC_FEATURE
<222> LOCATION: (89)..(89)
<223> OTHER INFORMATION: Xaa is Ile or Val
<220> FEATURE:
<221> NAME/KEY: MISC_FEATURE
<222> LOCATION: (95)..(95)
<223> OTHER INFORMATION: Xaa is Ile or Leu
<220> FEATURE:
<221> NAME/KEY: MISC_FEATURE
<222> LOCATION: (99)..(99)
<223> OTHER INFORMATION: Xaa is Val or Gly
<220> FEATURE:
<221> NAME/KEY: MISC_FEATURE
<222> LOCATION: (114)..(114)
<223> OTHER INFORMATION: Xaa is Cys or Leu
<220> FEATURE:
<221> NAME/KEY: MISC_FEATURE
<222> LOCATION: (115)..(115)
<223> OTHER INFORMATION: Xaa is Ala or Ser
<220> FEATURE:
<221> NAME/KEY: MISC_FEATURE
<222> LOCATION: (116)..(116)
<223> OTHER INFORMATION: Xaa is Val or Met
<220> FEATURE:
<221> NAME/KEY: MISC_FEATURE
<222> LOCATION: (117)..(117)
<223> OTHER INFORMATION: Xaa is Val or Thr
<220> FEATURE:
<221> NAME/KEY: MISC_FEATURE
<222> LOCATION: (118)..(118)
<223> OTHER INFORMATION: Xaa is Arg or Cys
<220> FEATURE:
<221> NAME/KEY: MISC_FEATURE
<222> LOCATION: (122)..(122)
<223> OTHER INFORMATION: Xaa is Phe or Pro
<220> FEATURE:
<221> NAME/KEY: MISC_FEATURE
<222> LOCATION: (125)..(125)
<223> OTHER INFORMATION: Xaa is Leu or Val
<220> FEATURE:
<221> NAME/KEY: MISC_FEATURE
<222> LOCATION: (126)..(126)
<223> OTHER INFORMATION: Xaa is Ala or Val
<220> FEATURE:
<221> NAME/KEY: MISC_FEATURE
<222> LOCATION: (128)..(128)
<223> OTHER INFORMATION: Xaa is Ser or Ala
<220> FEATURE:
<221> NAME/KEY: MISC_FEATURE
<222> LOCATION: (133)..(133)
<223> OTHER INFORMATION: Xaa is Val or Leu or Met
<220> FEATURE:
<221> NAME/KEY: MISC_FEATURE
<222> LOCATION: (138)..(138)
<223> OTHER INFORMATION: Xaa is Lys or Arg
<220> FEATURE:
<221> NAME/KEY: MISC_FEATURE
<222> LOCATION: (139)..(139)
<223> OTHER INFORMATION: Xaa is Ser or Thr
<220> FEATURE:
<221> NAME/KEY: MISC_FEATURE
<222> LOCATION: (140)..(140)
<223> OTHER INFORMATION: Xaa is Val or Gly
<220> FEATURE:
<221> NAME/KEY: MISC_FEATURE
<222> LOCATION: (141)..(141)

<223> OTHER INFORMATION: Xaa is Gln or Glu
<220> FEATURE:
<221> NAME/KEY: MISC_FEATURE
<222> LOCATION: (143)..(143)
<223> OTHER INFORMATION: Xaa is Leu or Ser or Arg
<220> FEATURE:
<221> NAME/KEY: MISC_FEATURE
<222> LOCATION: (145)..(145)
<223> OTHER INFORMATION: Xaa is Ser or Phe
<220> FEATURE:
<221> NAME/KEY: MISC_FEATURE
<222> LOCATION: (147)..(147)
<223> OTHER INFORMATION: Xaa is Phe or Tyr
<220> FEATURE:
<221> NAME/KEY: MISC_FEATURE
<222> LOCATION: (148)..(148)
<223> OTHER INFORMATION: Xaa is Thr or Ala
<220> FEATURE:
<221> NAME/KEY: MISC_FEATURE
<222> LOCATION: (149)..(149)
<223> OTHER INFORMATION: Xaa is Ala or Ser
<220> FEATURE:
<221> NAME/KEY: MISC_FEATURE
<222> LOCATION: (150)..(150)
<223> OTHER INFORMATION: Xaa is Val or Ile
<220> FEATURE:
<221> NAME/KEY: MISC_FEATURE
<222> LOCATION: (151)..(151)
<223> OTHER INFORMATION: Xaa is Thr or Cys
<220> FEATURE:
<221> NAME/KEY: MISC_FEATURE
<222> LOCATION: (152)..(152)
<223> OTHER INFORMATION: Xaa is Asn or Ser
<220> FEATURE:
<221> NAME/KEY: MISC_FEATURE
<222> LOCATION: (153)..(153)
<223> OTHER INFORMATION: Xaa is Phe or Val
<220> FEATURE:
<221> NAME/KEY: MISC_FEATURE
<222> LOCATION: (156)..(156)
<223> OTHER INFORMATION: Xaa is Ser or Asp
<220> FEATURE:
<221> NAME/KEY: MISC_FEATURE
<222> LOCATION: (157)..(157)
<223> OTHER INFORMATION: Xaa is Leu or Val
<220> FEATURE:
<221> NAME/KEY: MISC_FEATURE
<222> LOCATION: (164)..(164)
<223> OTHER INFORMATION: Xaa is Asn or Gln
<220> FEATURE:
<221> NAME/KEY: MISC_FEATURE
<222> LOCATION: (179)..(179)
<223> OTHER INFORMATION: Xaa is Val or Ile

<400> SEQUENCE: 8

```
Ser Xaa Leu Ser Trp Leu Ser Leu Asp Val Ser Ala Ala Phe Tyr His
1               5                   10                  15

Xaa Pro Leu His Pro Ala Ala Met Pro His Leu Leu Xaa Gly Ser Ser
            20                  25                  30

Gly Leu Xaa Arg Tyr Val Ala Arg Leu Ser Ser Xaa Ser Xaa Xaa Xaa
        35                  40                  45

Asn Xaa Gln Xaa Xaa Xaa Xaa Xaa Xaa Leu His Xaa Xaa Cys Ser Arg
    50                  55                  60

Xaa Leu Tyr Val Ser Leu Xaa Leu Leu Tyr Xaa Thr Xaa Gly Xaa Lys
65                  70                  75                  80

Leu His Leu Xaa Xaa His Pro Ile Xaa Leu Gly Phe Arg Lys Xaa Pro
                85                  90                  95

Met Gly Xaa Gly Leu Ser Pro Phe Leu Leu Ala Gln Phe Thr Ser Ala
            100                 105                 110

Ile Xaa Xaa Xaa Xaa Xaa Arg Ala Phe Xaa His Cys Xaa Xaa Phe Xaa
        115                 120                 125
```

-continued

```
Tyr Met Asp Asp Xaa Val Leu Gly Ala Xaa Xaa Xaa Xaa His Xaa Glu
    130                 135                 140

Xaa Leu Xaa Xaa Xaa Xaa Xaa Xaa Xaa Leu Leu Xaa Xaa Gly Ile His
145                 150                 155                 160

Leu Asn Pro Xaa Lys Thr Lys Arg Trp Gly Tyr Ser Leu Asn Phe Met
                165                 170                 175

Gly Tyr Xaa Ile Gly
            180


<210> SEQ ID NO 9
<211> LENGTH: 13
<212> TYPE: PRT
<213> ORGANISM: Hepatitis B virus
<220> FEATURE:
<221> NAME/KEY: MISC_FEATURE
<222> LOCATION: (1)..(1)
<223> OTHER INFORMATION: Xaa is S or D
<220> FEATURE:
<221> NAME/KEY: MISC_FEATURE
<222> LOCATION: (2)..(2)
<223> OTHER INFORMATION: Xaa is L or V
<220> FEATURE:
<221> NAME/KEY: MISC_FEATURE
<222> LOCATION: (9)..(9)
<223> OTHER INFORMATION: Xaa is N or Q

<400> SEQUENCE: 9

Xaa Xaa Gly Ile His Leu Asn Pro Xaa Lys Thr Lys Arg
1               5                   10


<210> SEQ ID NO 10
<211> LENGTH: 4
<212> TYPE: PRT
<213> ORGANISM: Hepatitis B virus

<400> SEQUENCE: 10

Tyr Met Asp Asp
1
```

VIRAL VARIANTS

This application is a continuation of application Ser. No. 09/958,503, filed Nov. 27, 2001 (now U.S. Pat. No. 7,291,453), which is a U.S. National Phase of International Application No. PCT/AU00/00294, filed Apr. 7, 2000, which designated the U.S. and claims benefit of Australian Patent Application No. PP 9679, filed Apr. 9, 1999, the entire contents of each of which are hereby incorporated by reference in this application.

FIELD OF THE INVENTION

The present invention relates generally to viral variants exhibiting reduced sensitivity to particular agents and/or reduced interactivity with immunological reagents. More particularly, the present invention is directed to hepatitis B virus variants exhibiting complete or partial resistance to nucleoside analogues and/or reduced interactivity with antibodies to viral surface components including reduced sensitivity. The present invention further contemplates assays for detecting such viral variants which assays are useful in monitoring anti-viral therapeutic regimes and in developing new or modified vaccines directed against viral agents and in particular hepatitis B virus variants.

BACKGROUND OF THE INVENTION

Bibliographic details of the publications numerically referred to in this specification are collected at the end of the description.

Specific mutations in an amino acid sequence are represented herein as $AXaa_1nXaa_2$" where $Xaa_1$ is the original amino acid residue before mutation, n is the residue number and $Xaa_2$ is the mutant amino acid. The abbreviation "Xaa" may be the three letter or single letter (i.e. "X") code. The amino acid residues for Hepatitis B virus DNA polymerase are numbered with the residue methionine in the motif Tyr Met Asp Asp (YMDD (SEQ ID NO:10)) being residue number 550. Hepatitis B virus (HBV) can cause debilitating disease conditions and can lead to acute liver failure. HBV is a DNA virus which replicates via an RNA intermediate and utilizes reverse transcription in its replication strategy (1). The HBV genome is of a complex nature having a partially double stranded DNA structure with overlapping open reading frames encoding surface, core, polymerase and X genes. The complex nature of the HBV genome is represented in FIG. 1.

The presence of an HBV DNA polymerase has led to the proposition that nucleoside analogues could act as effective anti-viral agents. Examples of nucleoside analogues currently being tested are penciclovir and its oral form famciclovir (2, 3, 4, 5), lamivudine (6,7). Adefovir has been shown to have effective anti-HBV activity in vitro. Generally, such nucleotide analogues are used in conjunction with Hepatitis B immunoglobulin (HBIG) therapy. There is potential for such agents to be used in the treatment of chronic HBV infection.

Penciclovir has been shown to have potent inhibitory activity against duck HBV DNA synthesis in vitro and has been shown to inhibit HBV DNA polymerase-reverse transcriptase activity in vitro (8,9). Similarly, oral famiciclovir has been demonstrated to inhibit intra-hepatic replication of duck HBV virus in vivo (10). In man, famciclovir has been shown to reduce HBV DNA replication in a patient with severe hepatitis B following orthotopic liver transplantation (OLT) (11).

In work leading up to the present invention, nucleoside analogue antiviral therapy was used to control severe post-OLT recurrence of HBV infection (12). Long term therapy is mandatory where patients are immunosuppressed and the rate of HBV replication is very high. However, under such conditions, as with any long term chemotherapy of infectious agents, there is a potential for development of resistance or reduced sensitivity to the therapeutic agents employed. In addition, some patients do not respond to famciclovir pre-OLT. This may be due to patients not metabolising famciclovir or patients infected with a famciclovir-resistant HBV variant.

In accordance with the present invention, the inventors have identified variants of HBV with mutations in the HBV DNA polymerase gene which to varying extents reduce the sensitivity of HBV to nucleoside analogues. The identification of these HBV variants is important for the development of assays to monitor nucleoside analogue therapeutic regimes and to screen for agents which can mask the effects of the mutation, i.e. in the development of new vaccines. In addition, since the HBV genome comprises a series of overlapping open reading frames, a nucleotide mutation in one open reading frame can affect translation products in another open reading frame. In further accordance with the present invention, the inventors have observed mutations which reduce the interactivity of immunological reagents, such as antibodies and immune cells, to viral surface components. Such viral variants are referred to herein as "escape mutants" since they potentially escape existing immunological memory.

SUMMARY OF THE INVENTION

Throughout this specification, unless the context requires otherwise, the word Acomprise≅, or variations such as Acomprises≅ or Acomprising≅, will be understood to imply the inclusion of a stated element or integer or group of elements or integers but not the exclusion of any other element or integer or group of elements or integers.

Nucleotide and amino acid sequences are referred to by a sequence identifier, i.e. SEQ ID NO:1, SEQ ID NO:2, etc. A sequence listing is provided after the claims.

One aspect of the present invention is directed to a variant of an isolated DNA virus which replicates via an RNA intermediate wherein said variant comprises a nucleotide mutation in a gene encoding a DNA polymerase resulting in at least one amino acid addition, substitution and/or deletion to said DNA polymerase.

Another aspect of the present invention provides a variant of an isolated DNA virus which replicates via an RNA intermediate wherein said variant comprises a nucleotide mutation in a gene encoding a viral surface component resulting in at least one amino acid addition, substitution and/or deletion in said viral surface component.

Still a further aspect of the present invention is directed to a variant of an isolated DNA virus which replicates via an RNA intermediate at least wherein said variant comprises a nucleotide mutation in an overlapping portion of at least two open reading frames resulting in an amino acid addition, substitution and/or deletion to translation products of said open reading frames.

Still yet a further aspect of the present invention provides an HBV variant comprising a mutation in the nucleotide sequence encoding a DNA polymerase resulting in an amino acid addition, substitution and/or deletion in said DNA polymerase in one or more amino acids as set forth in Formula I (SEQ ID NO:7):

| FORMULA I |
|---|
| S $Z_1$ L S W L S L D V S A A F Y H $Z_2$ P L H P A A M |
| P H L L $Z_3$ G S S G L $Z_4$ R Y V A R L S S $Z_5$ S $Z_6$ $Z_7$ |
| X N $Z_8$ Q $Z_9$ $Z_{10}$ X X X $Z_{11}$ L H $Z_{12}$ $Z_{13}$ C S R $Z_{14}$ L Y V |
| S L $Z_{15}$ L L Y $Z_{16}$ T $Z_{17}$ G $Z_{18}$ K L H L $Z_{19}$ $Z_{20}$ H P |
| I $Z_{21}$ L G F R K $Z_{22}$ P M G $Z_{23}$ G L S P F L L A Q F |
| T S A I $Z_{24}$ $Z_{25}$ $Z_{26}$ $Z_{27}$ $Z_{28}$ R A F $Z_{29}$ H C $Z_{30}$ |
| $Z_{31}$ F $Z_{32}$ Y M* D D $Z_{33}$ V L G A $Z_{34}$ $Z_{35}$ $Z_{36}$ $Z_{37}$ H |
| $Z_{38}$ E $Z_{39}$ L $Z_{40}$ $Z_{41}$ $Z_{42}$ $Z_{43}$ $Z_{44}$ $Z_{45}$ $Z_{46}$ L L $Z_{47}$ |
| $Z_{48}$ G I H L N P $Z_{49}$ K T K R W G Y S L N F M G Y |
| $Z_{50}$ I G |

wherein:
X is any amino acid;
$Z_1$ is N or D;
$Z_2$ is I or P;
$Z_3$ is I or V;
$Z_4$ is S or D;
$Z_5$ is T or N;
$Z_6$ is R or N;
$Z_7$ is N or I;
$Z_8$ is N or Y or H;
$Z_9$ is H or Y;
$Z_{10}$ is G or R;
$Z_{11}$ is D or N;
$Z_{12}$ is D or N;
$Z_{13}$ is S or Y;
$Z_{14}$ is N or Q;
$Z_{15}$ is L or M;
$Z_{16}$ is K or Q;
$Z_{17}$ is Y or F;
$Z_{18}$ is R or W;
$Z_{19}$ is Y or L;
$Z_{20}$ is S or A;
$Z_{21}$ is I or V;
$Z_{22}$ is I or L;
$Z_{23}$ is V or G;
$Z_{24}$ is C or L;
$Z_{25}$ is A or S;
$Z_{26}$ is V or M;
$Z_{27}$ is V or T;
$Z_{28}$ is R or C;
$Z_{29}$ is F or P;
$Z_{30}$ is L or V;
$Z_{31}$ is A or V;
$Z_{32}$ is S or A;
$Z_{33}$ is V or L or M;
$Z_{34}$ is K or R;
$Z_{35}$ is S or T;
$Z_{36}$ is V or G;
$Z_{37}$ is Q or E;
$Z_{38}$ is L or S or R;
$Z_{39}$ is S or F;
$Z_{40}$ is F or Y;
$Z_{41}$ is T or A;
$Z_{42}$ is A or S;
$Z_{43}$ is V or I;
$Z_{44}$ is T or C;
$Z_{45}$ is N or S;
$Z_{46}$ is F or V;
$Z_{47}$ is S or D;
$Z_{48}$ is L or V;
$Z_{49}$ is N or Q;
$Z_{50}$ is V or I; and
M* is amino acid 550
provided said mutation is not in the YMDD (SEQ ID NO:10) motif of the C domain alone, and wherein said variant exhibits decreased sensitivity to a nucleoside analogue.

Another aspect of the present invention contemplates an HBV variant comprising a mutation in the nucleotide sequence encoding a viral surface component resulting in an amino acid addition, substitution and/or deletion in said viral surface component in a region corresponding to the amino acid sequence set forth in Formula I wherein said variant exhibits decreased interactivity of immunological reagents to said viral surface component.

Yet another aspect of the present invention provides an HBV variant comprising a mutation in the nucleotide sequence encoding a viral surface component resulting in an amino acid addition, substitution and/or addition in said viral surface component in a region defined by amino acids 67-226 of the HBV surface antigen or functionally equivalent region wherein said variant exhibits decreased interactivity of immunological reagents to said viral surface component.

Still another aspect of the present invention provides an HBV variant comprising a mutation in an overlapping open reading frame in its genome wherein said mutation is in a region defined by one or more of domains F and A through E of HBV DNA polymerase provided that it is not in the YMDD (SEQ ID NO:10) motif of the C domain alone; and in the overlapping region corresponding to amino acids 67-226 of HBV surface antigen; and wherein said variant exhibits decreased sensitivity to a nucleotide analogue and exhibits decreased interactivity to immunological reagents specific to HBV surface antigens.

Still yet another aspect of the present invention contemplates a method for determining the potential for an HBV to exhibit reduced sensitivity to a nucleoside analogue, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase wherein the presence of such a mutation is an indication of the likelihood of resistance to said nucleoside analogue.

Even still another aspect of the present invention provides a method for determining the potential for an HBV to exhibit reduced interactivity to antibody to HBV surface antigen, said method comprising isolating DNA or corresponding mRNA from said HBV and screening for a mutation in the nucleotide sequence encoding HBV surface antigen resulting in at least one amino acid substitution, deletion and/or addition in amino acids 67 to 226 of said surface antigen or a region proximal thereto of said surface antigen wherein the presence of such a mutation is an indication of the likelihood of reducing interactivity of said antibodies to said mutated surface antigen.

Another aspect of the present invention contemplates method for determining whether an HBV isolate encodes a variant DNA polymerase, said method comprising determining the amino acid sequence of its DNA polymerase directly or via a nucleotide sequence and comparing same to the amino acid sequence below (SEQ ID NO:7):

| FORMULA I |
| --- |
| S $Z_1$ L S W L S L D V S A A F Y H $Z_2$ P L H P A A M |
| P H L L $Z_3$ G S S G L $Z_4$ R Y V A R L S S $Z_5$ S $Z_6$ $Z_7$ |
| X N $Z_8$ Q $Z_9$ $Z_{10}$ X X X $Z_{11}$ L H $Z_{12}$ $Z_{13}$ C S R $Z_{14}$ L Y V |
| S L $Z_{15}$ L L Y $Z_{16}$ T $Z_{17}$ G $Z_{18}$ K L H L $Z_{19}$ $Z_{20}$ H P |
| I $Z_{21}$ L G F R K $Z_{22}$ P M G $Z_{23}$ G L S P F L L A Q F |
| T S A I $Z_{24}$ $Z_{25}$ $Z_{26}$ $Z_{27}$ $Z_{28}$ R A F $Z_{29}$ H C $Z_{30}$ |
| $Z_{31}$ F $Z_{32}$ Y M* D D $Z_{33}$ V L G A $Z_{34}$ $Z_{35}$ $Z_{36}$ $Z_{37}$ H |
| $Z_{38}$ E $Z_{39}$ L $Z_{40}$ $Z_{41}$ $Z_{42}$ $Z_{43}$ $Z_{44}$ $Z_{45}$ $Z_{46}$ L L $Z_{47}$ |
| $Z_{48}$ G I H L N P $Z_{49}$ K T K R W G Y S L N F M G Y |
| $Z_{50}$ I G |

wherein:
X is any amino acid;
$Z_1$ is N or D;
$Z_2$ is I or P;
$Z_3$ is I or V;
$Z_4$ is S or D;
$Z_5$ is T or N;
$Z_6$ is R or N;
$Z_7$ is N or L;
$Z_8$ is N or Y or H;
$Z_9$ is H or Y;
$Z_{10}$ is G or R;
$Z_{11}$ is D or N;
$Z_{12}$ is D or N;
$Z_{13}$ is S or Y;
$Z_{14}$ is N or Q;
$Z_{15}$ is L or M;
$Z_{16}$ is K or Q;
$Z_{17}$ is Y or F;
$Z_{18}$ is R or W;
$Z_{19}$ is Y or L;
$Z_{20}$ is S or A;
$Z_{21}$ is I or V;
$Z_{22}$ is I or L;
$Z_{23}$ is V or G;
$Z_{24}$ is C or L;
$Z_{25}$ is A or S;
$Z_{26}$ is V or M;
$Z_{27}$ is V or T;
$Z_{28}$ is R or C;
$Z_{29}$ is F or P;
$Z_{30}$ is L or V;
$Z_{31}$ is A or V;
$Z_{32}$ is S or A;
$Z_{33}$ is V or L or M;
$Z_{34}$ is K or R;
$Z_{35}$ is S or T;
$Z_{36}$ is V or G;
$Z_{37}$ is Q or E;
$Z_{38}$ is L or S or R;
$Z_{39}$ is S or F;
$Z_{40}$ is F or Y;
$Z_{41}$ is T or A;
$Z_{42}$ is A or S;
$Z_{43}$ is V or I;
$Z_{44}$ is T or C;
$Z_{45}$ is N or S;
$Z_{46}$ is F or V;
$Z_{47}$ is S or D;
$Z_{48}$ is L or V;
$Z_{49}$ is N or Q;
$Z_{50}$ is V or I; and
M* is amino acid 550.

Yet another aspect of the present invention is directed to an isolated variant HBV surface antigen or a recombinant or derivative form thereof or a chemical equivalent thereof wherein said surface antigen or its recombinant or derivative form or its chemical equivalent exhibits an altered immunological profile compared to a surface antigen from a reference HBV.

Still another aspect of the present invention provides an HBV vaccine containing one or more HBV variants carrying mutations which alter the surface antigen (not including G145R).

Yet another aspect of the present invention provides a composition comprising a variant HBV or an HBV surface antigen from said variant HBV or a recombinant or derivative form thereof or its chemical equivalent and one or more pharmaceutically acceptable carriers or diluents.

Still yet another aspect of the present invention provides a use of a variant of an isolated DNA virus which replicates via an RNA intermediate wherein said variant comprises a nucleotide mutation in a gene encoding a DNA polymerase resulting in at least one amino acid addition, substitution and/or deletion to said DNA polymerase in the manufacture of a medicament for the treatment and/or prophylaxis of hepatitis.

Even still yet another aspect of the present invention provides a use of a variant of an isolated DNA virus which replicates via an RNA intermediate wherein said variant comprises a nucleotide mutation in a gene encoding a viral surface component resulting in at least one amino acid addition, substitution and/or deletion in said viral surface component in the manufacture of a medicament for the treatment and/or prophylaxis of hepatitis.

Another aspect of the present invention provides a use of a variant of an isolated DNA virus which replicates via an RNA intermediate wherein said variant comprises a nucleotide mutation in an overlapping portion of at least two open reading frames resulting in an amino acid addition, substitution and/or deletion to translation products of said open reading frames in the manufacture of a medicament for the treatment and/or prophylaxis of hepatitis.

BRIEF DESCRIPTION OF THE FIGURES

FIG. 2 is a representation showing conserved regions of domain A to E (underlined) of HBV (SEQ ID NO:7). M in YMDD (SEQ ID NO:10) is designated amino acid number 550. * indicates greater than three amino acid possibilities at this position of the consensus sequence.

DETAILED DESCRIPTION OF THE PREFERRED EMBODIMENTS

Figure 1:
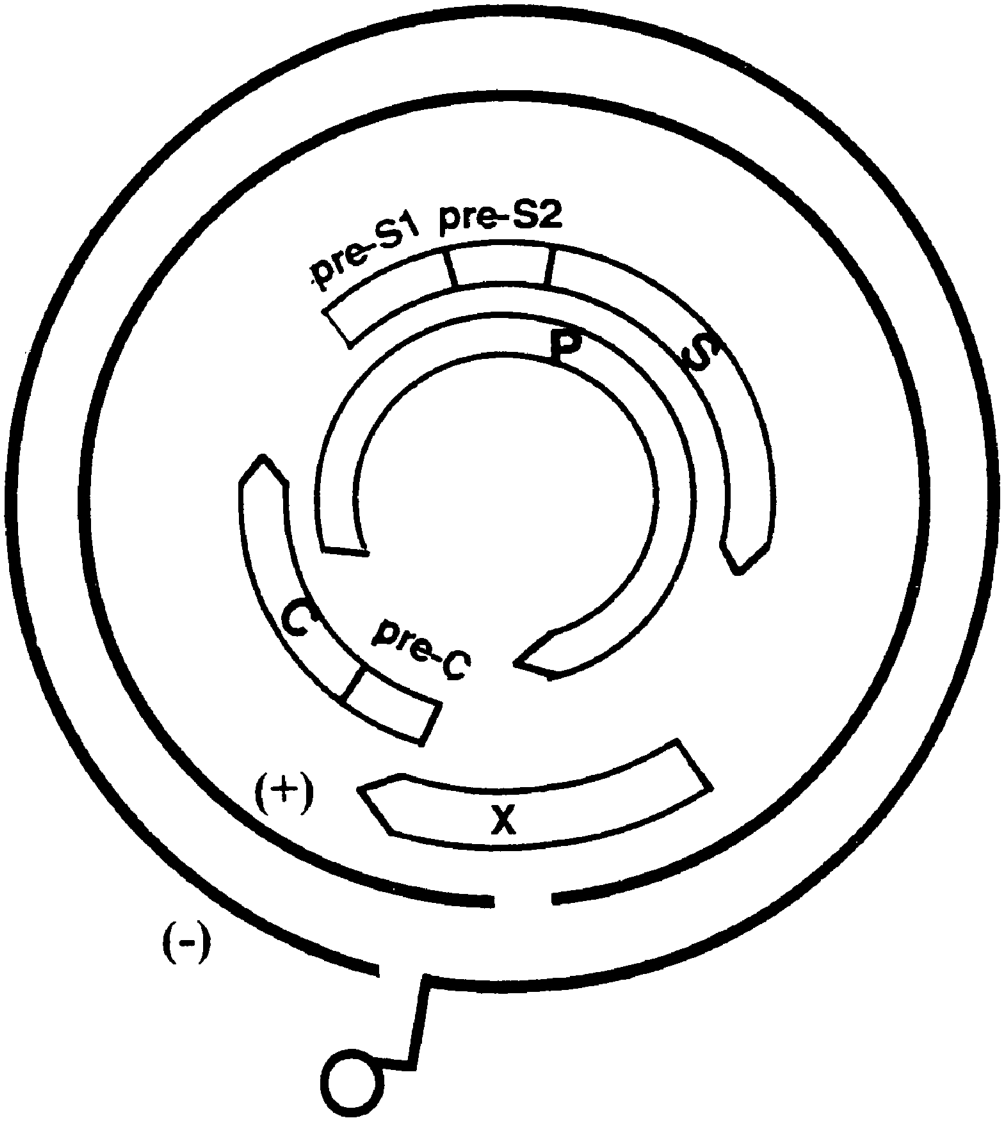
FIG. 1 is a diagrammatic representation showing the partially double stranded DNA HBV genome showing the overlapping open reading frames encoding surface (S), core (C), polymerase (P) and X gene.

Accordingly, one aspect of the present invention is directed to a variant of an isolated DNA virus which replicates via an RNA intermediate wherein said variant comprises a nucleotide mutation in a gene encoding a DNA polymerase resulting in at least one amino acid addition, substitution and/or deletion to said DNA polymerase.

Another aspect of the present invention provides a variant of an isolated DNA virus which replicates via an RNA intermediate wherein said variant comprises a nucleotide mutation in a gene encoding a viral surface component resulting in at least one amino acid addition, substitution and/or deletion in said viral surface component.

Still a further aspect of the present invention is directed to a variant of an isolated DNA virus which replicates via an RNA intermediate at least wherein said variant comprises a nucleotide mutation in an overlapping portion of at least two open reading frames resulting in an amino acid addition, substitution and/or deletion to translation products of said open reading frames.

Preferably, the DNA virus is a hepatitis virus or a related virus and is most preferably HBV.

A Arelated virus≅ in accordance with the present invention is one related at the genetic, immunological, epidemiological and/or biochemical levels.

Preferably, the mutation in the DNA polymerase results in decreased sensitivity of the HBV to a nucleoside analogue.

Preferably, the mutation in the viral surface component reduces the interactivity of immunological reagents such as antibodies and immune cells to the viral surface component. Most preferably, the viral surface component is a viral surface antigen. The reduction in the interactivity of immunological reagents to a viral surface component generally includes the absence of immunological memory to recognize or substantially recognize the viral surface component.

A viral variant may, in accordance with a preferred aspect of the present invention, carry mutation only in the DNA polymerase or the surface antigen or may carry a mutation in both molecules. The term Amutation≅ is to be read in its broadest context and includes a silent mutation not substantially affecting the normal function of the DNA polymerase or surface antigen or may be an active mutation having the effect of selection of nucleoside analogue resistance or an escape mutant phenotype. Where multiple mutations occur in accordance with the present invention or where multiple phenotypes result from a single mutation, at least one mutation must be active or the virus must exhibit at least one altered phenotype such as nucleoside analogue resistance or reduced immunological interactivity to the surface antigen.

Regions of the HBV polymerase show amino acid similarity with other RNA-dependent DNA polymerases and RNA-dependent polymerases (13). The present invention extends to all domains of the HBV DNA polymerase and in particular regions F and A through E. In this specification, reference is particularly made to the conserved regions defined by Poch et al. (13) as domains A to E (see also reference 18). Regions A to E are defined by the amino acid sequence set forth in Formula I below:

| FORMULA I |
|---|
| S $Z_1$ L S W L S L D V S A A F Y H $Z_2$ P L H P A A M |
| P H L L $Z_3$ G S S G L $Z_4$ R Y V A R L S S $Z_5$ S $Z_6$ $Z_7$ |
| X N $Z_8$ Q $Z_9$ $Z_{10}$ X X X $Z_{11}$ L H $Z_{12}$ $Z_{13}$ C S R $Z_{14}$ L Y V |
| S L $Z_{15}$ L L Y $Z_{16}$ T $Z_{17}$ G $Z_{18}$ K L H L $Z_{19}$ $Z_{20}$ H P |
| I $Z_{21}$ L G F R K $Z_{22}$ P M G $Z_{23}$ G L S P F L L A Q F |

-continued

| FORMULA I |
|---|
| T S A I $Z_{24}$ $Z_{25}$ $Z_{26}$ $Z_{27}$ $Z_{28}$ R A F $Z_{29}$ H C $Z_{30}$ |
| $Z_{31}$ F $Z_{32}$ Y M* D D $Z_{33}$ V L G A $Z_{34}$ $Z_{35}$ $Z_{36}$ $Z_{37}$ H |
| $Z_{38}$ E $Z_{39}$ L $Z_{40}$ $Z_{41}$ $Z_{42}$ $Z_{43}$ $Z_{44}$ $Z_{45}$ $Z_{46}$ L L $Z_{47}$ |
| $Z_{48}$ G I H L N P $Z_{49}$ K T K R W G Y S L N F M G Y |
| $Z_{50}$ I G |

wherein:

X is any amino acid;
$Z_1$ is N or D;
$Z_2$ is I or P;
$Z_3$ is I or V;
$Z_4$ is S or D;
$Z_5$ is T or N;
$Z_6$ is R or N;
$Z_7$ is N or I;
$Z_8$ is N or Y or H;
$Z_9$ is H or Y;
$Z_{10}$ is G or R;
$Z_{11}$ is D or N;
$Z_{12}$ is D or N;
$Z_{13}$ is S or Y;
$Z_{14}$ is N or Q;
$Z_{15}$ is L or M;
$Z_{16}$ is K or Q;
$Z_{17}$ is Y or F;
$Z_{18}$ is R or W;
$Z_{19}$ is Y or L;
$Z_{20}$ is S or A;
$Z_{21}$ is I or V;
$Z_{22}$ is I or L;
$Z_{23}$ is V or G;
$Z_{24}$ is C or L;
$Z_{25}$ is A or S;
$Z_{26}$ is V or M;
$Z_{27}$ is V or T;
$Z_{28}$ is R or C;
$Z_{29}$ is F or P;
$Z_{30}$ is L or V;
$Z_{31}$ is A or V;
$Z_{32}$ is S or A;
$Z_{33}$ is V or L or M;
$Z_{34}$ is K or R;
$Z_{35}$ is S or T;
$Z_{36}$ is V or G;
$Z_{37}$ is Q or E;
$Z_{38}$ is L or S or R;
$Z_{39}$ is S or F;
$Z_{40}$ is F or Y;
$Z_{41}$ is T or A;
$Z_{42}$ is A or S;
$Z_{43}$ is V or I;
$Z_{44}$ is T or C;
$Z_{45}$ is N or S;
$Z_{46}$ is F or V;
$Z_{47}$ is S or D;
$Z_{48}$ is L or V;
$Z_{49}$ is N or Q;
$Z_{50}$ is V or I; and
M* is amino acid 550.

Preferably, the mutation results in an altered amino acid sequence in any one or more of domains F and A through E or regions proximal thereto of the HBV DNA polymerase. The present invention does not extend to a mutation alone in the YMDD (SEQ ID NO:10) motif of the C domain of the HBV DNA polymerase although such a mutation is contemplated by the present invention if it occurs in combination with one or more mutations in another location.

The mutation in the viral surface component is preferably in one or more amino acid residues within the major hydrophilic regions of the protein, and in particular within the amino acid sequence 67-226 of the HBV viral surface antigen.

According to a preferred aspect of the present invention, there is provided an HBV variant comprising a mutation in the nucleotide sequence encoding a DNA polymerase resulting in an amino acid addition, substitution and/or deletion in said DNA polymerase in one or more amino acids as set forth in Formula I:

FORMULA I

S $Z_1$ L S W L S L D V S A A F Y H $Z_2$ P L H P A A M

P H L L $Z_3$ G S S G L $Z_4$ R Y V A R L S S $Z_5$ S $Z_6$ $Z_7$

X N $Z_8$ Q $Z_9$ $Z_{10}$ X X X $Z_{11}$ L H $Z_{12}$ $Z_{13}$ C S R $Z_{14}$ L Y V

S L $Z_{15}$ L L Y $Z_{16}$ T $Z_{17}$ G $Z_{18}$ K L H L $Z_{19}$ $Z_{20}$ H P

I $Z_{21}$ L G F R K $Z_{22}$ P M G $Z_{23}$ G L S P F L L A Q F

T S A I $Z_{24}$ $Z_{25}$ $Z_{26}$ $Z_{27}$ $Z_{28}$ R A F $Z_{29}$ H C $Z_{30}$ $Z_{31}$ F $Z_{32}$ Y M* D D $Z_{33}$ V L G A $Z_{34}$ $Z_{35}$ $Z_{36}$ $Z_{37}$ H $Z_{38}$ E $Z_{39}$ L $Z_{40}$ $Z_{41}$ $Z_{42}$ $Z_{43}$ $Z_{44}$ $Z_{45}$ $Z_{46}$ L L $Z_{47}$ $Z_{48}$ G I H L N P $Z_{49}$ K T K R W G Y S L N F M G Y $Z_{50}$ I G wherein:
X is any amino acid;
$Z_1$ is N or D;
$Z_2$ is I or P;
$Z_3$ is I or V;
$Z_4$ is S or D;
$Z_5$ is T or N;
$Z_6$ is R or N;
$Z_7$ is N or I;
$Z_8$ is N or Y or H;
$Z_9$ is H or Y;
$Z_{10}$ is G or R;
$Z_{11}$ is D or N;
$Z_{12}$ is D or N;
$Z_{13}$ is S or Y;
$Z_{14}$ is N or Q;
$Z_{15}$ is L or M;
$Z_{16}$ is K or Q;
$Z_{17}$ is Y or F;
$Z_{18}$ is R or W;
$Z_{19}$ is Y or L;
$Z_{20}$ is S or A;
$Z_{21}$ is I or V;
$Z_{22}$ is I or L;
$Z_{23}$ is V or G;
$Z_{24}$ is C or L;
$Z_{25}$ is A or S;
$Z_{26}$ is V or M;
$Z_{27}$ is V or T;
$Z_{28}$ is R or C;
$Z_{29}$ is F or P;
$Z_{30}$ is L or V;
$Z_{31}$ is A or V;
$Z_{32}$ is S or A;
$Z_{33}$ is V or L or M;
$Z_{34}$ is K or R;
$Z_{35}$ is S or T;
$Z_{36}$ is V or G;
$Z_{37}$ is Q or E;
$Z_{38}$ is L or S or R;
$Z_{39}$ is S or F;
$Z_{40}$ is F or Y;
$Z_{41}$ is T or A;
$Z_{42}$ is A or S;
$Z_{43}$ is V or I;
$Z_{44}$ is T or C;
$Z_{45}$ is N or S;
$Z_{46}$ is F or V;
$Z_{47}$ is S or D;
$Z_{48}$ is L or V;
$Z_{49}$ is N or Q;
$Z_{50}$ is V or I; and
M* is amino acid 550
provided said mutation is not in the YMDD (SEQ ID NO:10) motif of the C domain alone, and wherein said variant exhibits decreased sensitivity to a nucleoside analogue.

Another preferred aspect of the present invention contemplates an HBV variant comprising a mutation in the nucleotide sequence encoding a viral surface component resulting in an amino acid addition, substitution and/or deletion in said viral surface component in a region corresponding to the amino acid sequence set forth in Formula I wherein said variant exhibits decreased interactivity of immunological reagents to said viral surface component.

Yet another preferred aspect of the present invention relates to an HBV variant comprising a mutation in the nucleotide sequence encoding a viral surface component resulting in an amino acid addition, substitution and/or addition in said viral surface component in a region defined by amino acids 67-226 of the HBV surface antigen or functionally equivalent region wherein said variant exhibits decreased interactivity of immunological reagents to said viral surface component.

Still yet another aspect of the present invention is directed to an HBV variant comprising a mutation in an overlapping open reading frame in its genome wherein said mutation is in a region defined by one or more of domains F and A through E of HBV DNA polymerase provided that it is not in the YMDD (SEQ ID NO:10) motif of the C domain alone; and in the overlapping region corresponding to amino acids 67 to 226 of HBV surface antigen and wherein said variant exhibits decreased sensitivity to a nucleotide analogue and exhibits decreased interactivity to immunological reagents specific to HBV surface antigens.

One particular mutant is M550I/V which has been previously described following lamivudine treatment. The present invention does not extend to this mutant in so far as it arises following treatment with lamuvidine alone. An M550V mutant is selected in conjunction with the mutation L526M and this is also not within the scope of the present invention.

The present invention does not extend to the following lamuvidine resistance mutations when selected by lamuvidine treatment alone, however, it does extend to these mutations when selected during famciclovir (FCV) treatment:

L428M, T481C, T496A, L497F, V509I, V519L, L526M, T530S, A546V, F548V, M550I, V553I, S559T, Q561H, S565A, A568T, 1570S, L575M, L581I and N584S (16, 29, 30, 31, 32, 33, 34, 35, 36, 37, 40, 41, 42, 45).

Furthermore, the present invention does not extend to the following published famciclovir selected mutations:

S424T, Del 462-468, I509V, V519L, P523L, L526M, L526V, A528T, T530S, V553I, S565A, I570V and N594H (38, 39, 41, 43, 44, 46).

The viral variant exhibiting reduced interactivity to immunological reagents is an escape mutant since antibodies or other immunological response to HBV from a prior exposure to the virus or following vaccination are no longer effective in targeting a viral surface component since the mutation has altered a B- and/or T-cell epitope on the surface antigen.

Reduced or decreased sensitivity to nucleotide, analogue or immunological agents is also encompassed by the term Aresistance≅. The term Aresistance≅ is used in its most general sense and includes total resistance or partial resistance or decreased sensitivity to a nucleoside analogue.

Preferably, the variants are in isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV.

Preferred mutations in the HBV DNA polymerase and/or surface antigen include variants selected from patients following HBV recurrence following famciclovir and HBIG treatment, and patients who did not respond to famciclovir treatment as indicated by a decreased in HBV DNA and/or viral protein.

Preferred mutations in the HBV DNA polymerase together with corresponding mutation in the surface antigen (shown in parentheses) include one or more of the L423L/M/V (I168I/M), L423L/F (C69F/L), H436H/Y, H436Y, DEL 471-474 (DEL 117-120), S438T, W499E (D144E, G145R), I508V, V519L (E164D), L526M, S565A (S210R), N584S, N/S/H584N/K, R588R/K and N594H such as selected in patients with HBV recurrence following famciclovir and HBIG treatment; and H436N/H, S463S/Y (L109I/L), V537V/I (C/WI 82Y/STOP), V/G560E (Y206N), S/F 565A/S (S210R/S), S/F 565A (S210R), N/Q 584H, K587R and N594H, such as selected in patients who did not respond to famciclovir. Preferred mutations in the surface antigen include one or more of the following V96A, C138R, P142T/P, K160K/N and A194G/A after only hepatitis B virus immunoglobulin (HBIG) treatment. The term ADEL≅ means Adeletion≅ and ASTOP≅ means a stop codon.

The present invention does not extend to a mutation in the Hepatitis B surface antigen at G145R alone or in combination with D144E (23) when these mutations are selected without famciclovir treatment.

Particularly preferred mutations in the HBV DNA polymerase together with corresponding mutations in the surface antigen (shown in parentheses) include one or more of L423L/MV [I68I/M], H436H/Y, H436Y, DEL471-474 [DEL117-120], W499E [D144E and G145R], V519L [E164D], N/S/H 584 N/K and R588 R/K such as selected in patients with HBV recurrence following famciclovir and HBIG treatment; and H436H/N, S463 S/Y [L109I/L], V537 V/I [C/W 182 Y/STOP], and K587R, such as selected in non-responding patients following famciclovir treatment.

The identification of the variants of the present invention permits the generation of a range of assays to detect such variants. The detection of such variants may be important in identifying resistant variants to determine the appropriate form of chemotherapy and/or to monitor vaccination protocols, develop new or modified vaccine preparations.

Accordingly, another aspect of the present invention contemplates a method for determining the potential for an HBV to exhibit reduced sensitivity to a nucleoside analogue, said method comprising isolating DNA or corresponding mRNA from said HBV and screening for a mutation in the nucleotide sequence encoding HBV DNA polymerase resulting in at least one amino acid substitution, deletion and/or addition in any one or more of domains A through E or a region proximal thereto of said DNA polymerase wherein the presence of such a mutation is (an indication of the likelihood of resistance to said nucleoside analogue.

A further aspect of the present invention provides a method for determining the potential for an HBV to exhibit reduced interactivity to antibody to HBV surface antigen, said method comprising isolating DNA or corresponding mRNA from said HBV and screening for a mutation in the nucleotide sequence encoding HBV surface antigen resulting in at least one amino acid substitution, deletion and/or addition in amino acids 67 to 226 of said surface antigen or a region proximal thereto of said surface antigen wherein the presence of such a mutation is an indication of the likelihood of reducing interactivity of said antibodies to said mutated surface antigen.

Preferably, the assay detects one or more of the following mutations in the HBV DNA polymerase (with the corresponding mutation in the surface antigen shown in parentheses): L423L/M/V (I68I/M), L423L/F (C69F/L), H436H/Y, H436Y, DEL 471-474 (DEL 117-120), S438T, W499E (D144E, G145R), 1508V, V519L (E164D), L526M, S565A (S210R), N584S, N/S/H584N/K, R588R/K and N594H such as selected in patients with HBV recurrence following famciclovir and HBIG treatment; and H436N/H, S463S/Y (L109I/L), V537V/I (C/W182Y/STOP), V/G560E (Y206N), S/F 565A/S (S210R/S), S/F 565A (S210R), N/Q 584H, K587R and N594H, such as selected in patients who did not respond to famciclovir. Mutations may also be detected in the surface antigen including one or more of: V96A, C138R, P142T/P, K160KIN and A194G/A such as after Hepatitis B virus immunoglobulin (HBIG) treatment.

More particularly, the assay detects one or more of the following mutations in the HBV DNA polymerase (with corresponding mutations in the surface antigen shown in parentheses): L423L/MV [I68I/M], H436H/Y, H436Y, DEL471-474 [DEL117-120], W499E [D144E and G145R], V519L [E164D], N/S/H 584 N/K and R588 R/K such as selected in patients with HBV recurrence following famciclovir and HBIG treatment; and H436H/N, S463 S/Y [L109I/L], V537 V/I [C/W 182 Y/STOP], and K587R, such as selected in non-responding patients following famciclovir treatment.

The DNA or corresponding RNA may be assayed or alternatively the DNA polymerase or surface antigen may be screened for the mutation.

The detection according to this aspect of the invention may be any nucleic acid-based detection means, for example nucleic acid hybridisation techniques or polymerase chain reaction (PCR). The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR) and reverse transcription polymerase chain reaction (RT-PCR), amongst others.

The present invention extends to a range of immunologically based assays to detect variant HBV DNA polymerase or surface antigen. These assays are based on antibodies directed to naturally occurring HBV DNA polymerase or surface antigen which do not, or substantially do not, interact with the variant HBV DNA polymerase or surface antigen. Alternatively, antibodies to a variant HBV DNA polymerase or surface antigen are used which do not or substantially do not, interact with naturally occurring HBV DNA polymerase or surface antigen.

Monoclonal or polyclonal antibodies may be used although monoclonal antibodies are preferred as they can be produced in large quantity and in a homogenous form. A wide range of immunoassay techniques are available such as described in U.S. Pat. Nos. 4,016,043, 4,424,279 and 4,018,653.

The detection of amino acid variants of DNA polymerase is conveniently accomplished by reference to the consensus amino acid sequence shown in FIG. 2. The polymorphisms shown represent the variations shown in various data bases for active pathogenic HBV strains. Where an HBV variant comprises an amino acid different to what is represented, then such an isolate is considered a putative HBV variant having an altered DNA polymerase activity.

Accordingly, another aspect of the present invention contemplates a method for determining whether an HBV isolate encodes a variant DNA polymerase, said method comprising determining the amino acid sequence of its DNA polymerase directly or via a nucleotide sequence and comparing same to the amino acid sequence below:

| FORMULA I |
|---|
| S $Z_1$ L S W L S L D V S A A F Y H $Z_2$ P L H P A A M |
| P H L L $Z_3$ G S S G L $Z_4$ R Y V A R L S S $Z_5$ S $Z_6$ $Z_7$ |
| X N $Z_8$ Q $Z_9$ $Z_{10}$ X X X $Z_{11}$ L H $Z_{12}$ $Z_{13}$ C S R $Z_{14}$ L Y V |
| S L $Z_{15}$ L L Y $Z_{16}$ T $Z_{17}$ G $Z_{18}$ K L H L $Z_{19}$ $Z_{20}$ H P |
| I $Z_{21}$ L G F R K $Z_{22}$ P M G $Z_{23}$ G L S P F L L A Q F |
| T S A I $Z_{24}$ $Z_{25}$ $Z_{26}$ $Z_{27}$ $Z_{28}$ R A F $Z_{29}$ H C $Z_{30}$ |
| $Z_{31}$ F $Z_{32}$ Y M* D D $Z_{33}$ V L G A $Z_{34}$ $Z_{35}$ $Z_{36}$ $Z_{37}$ H |
| $Z_{38}$ E $Z_{39}$ L $Z_{40}$ $Z_{41}$ $Z_{42}$ $Z_{43}$ $Z_{44}$ $Z_{45}$ $Z_{46}$ L L $Z_{47}$ |
| $Z_{48}$ G I H L N P $Z_{49}$ K T K R W G Y S L N F M G Y |
| $Z_{50}$ I G |

wherein:
X is any amino acid;
$Z_1$ is N or D;
$Z_2$ is I or P;
$Z_3$ is I or V;
$Z_4$ is S or D;
$Z_5$ is T or N;
$Z_6$ is R or N;
$Z_7$ is N or I;
$Z_8$ is N or Y or H;
$Z_9$ is H or Y;
$Z_{10}$ is G or R;
$Z_{11}$ is D or N;
$Z_{12}$ is D or N;
$Z_{13}$ is S or Y;
$Z_{14}$ is N or Q;
$Z_{15}$ is L or M;
$Z_{16}$ is K or Q;
$Z_{17}$ is Y or F;
$Z_{18}$ is R or W;
$Z_{19}$ is Y or L;
$Z_{20}$ is S or A;
$Z_{21}$ is I or V;
$Z_{22}$ is I or L;
$Z_{23}$ is V or G;
$Z_{24}$ is C or L;
$Z_{25}$ is A or S;
$Z_{26}$ is V or M;
$Z_{27}$ is V or T;
$Z_{28}$ is R or C;
$Z_{29}$ is F or P;
$Z_{30}$ is L or V;
$Z_{31}$ is A or V;
$Z_{32}$ is S or A;
$Z_{33}$ is V or L or M;
$Z_{34}$ is K or R;
$Z_{35}$ is S or T;
$Z_{36}$ is V or G;
$Z_{37}$ is Q or E;
$Z_{38}$ is L or S or R;
$Z_{39}$ is S or F;
$Z_{40}$ is F or Y;
$Z_{41}$ is T or A;
$Z_{42}$ is A or S;
$Z_{43}$ is V or I;
$Z_{44}$ is T or C;
$Z_{45}$ is N or S;
$Z_{46}$ is F or V;
$Z_{47}$ is S or D;
$Z_{48}$ is L or V;
$Z_{49}$ is N or Q;
$Z_{50}$ is V or I; and
M* is amino acid 550.

The present invention further contemplates agents which mask the nucleoside analogue resistance mutation. Such agents will be particularly useful in long term treatment by nucleoside analogues. The agents may be DNA or RNA or proteinaceous or non-proteinaceous chemical molecules. Natural product screening such as from plants, coral and microorganisms is also contemplated as a useful potential source of masking agents. The agents may be in isolated form or in the form of a pharmaceutical composition and may be administered sequentially or simultaneously with the nucleoside analogue.

The present invention further extends to an isolated surface component from the HBV variants herein described. More particularly, the present invention provides an isolated surface antigen or a recombinant form thereof or derivative or chemical equivalent thereof. The isolated surface component and, more particularly, isolated surface antigen or its recombinant, derivative or chemical equivalents are useful in the development of biological compositions such as vaccine formulations.

Accordingly, another aspect of the present invention is directed to an isolated variant HBV surface antigen or a recombinant or derivative form thereof or a chemical equivalent thereof wherein said surface antigen or its recombinant or derivative form or its chemical equivalent exhibits an altered immunological profile compared to a surface antigen from a reference HBV. More particularly, the present invention provides an isolated variant HBV surface antigen or a recombinant or derivative form thereof or a chemical equivalent thereof wherein said HBV surface antigen or its recombinant or derivative form or its chemical equivalent comprises an amino acid sequence with a single or multiple amino acid substitution, addition and/or deletion or a truncation compared to an HBV surface antigen from a reference HBV and wherein a neutralising antibody directed to a reference HBV exhibits no or reduced neutralising activity to an HBV carrying said variant HBV surface antigen.

The present invention particularly contemplates an HBV vaccine containing one or more of the mutations which alter the surface antigen (not including G145R). Preferred mutations in the surface antigen and the HBV vaccine include one or more of I68I/M, C69F/L, H436Y, DEL 117-120, D144E, E164D, S210R, such as selected in patients with HBV recurrence following famciclovir and HBIG treatment; and L1091/L, C/W182Y/STOP, Y206N, S210R/S and S210R; such as selected in patients who do not respond to famciclovir. Variants carrying mutations in the surface antigen at V96A, C138R, P142T/P, K160K/N and/or A194G/A are particularly preferred.

The term "isolated" means the same as it does in relation to an isolated HBV variant.

As stated above, the present invention extends to derivatives and chemical equivalents (i.e. analogues) of the HBV surface component. Derivatives include single or multiple amino acid substitutions, additions and/or deletions to the HBV surface antigen. AAdditions≅ to amino acid sequences include fusions with other peptides, polypeptides or proteins or fusions to nucleotide sequences including fusions to other viral components.

Analogues of the variant HBV surface antigen contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues. These types of modifications are useful in stabilizing the immunointeractive molecules for use in diagnostic assays or in therapeutic protocols.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown below in Table 1. The inclusion of such unnatural amino acids or other derivations described herein may assist in stabilising the molecule in a vaccine composition.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| | | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
| | | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |

TABLE 1-continued

| Non-conventional amino acid | Code | Non-conventional amino acid | Code |
|---|---|---|---|
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

As stated above, these types of modifications may be important to stabilize the variant HBsAg molecule if administered to an individual or for use as a diagnostic reagent.

Other derivatives contemplated by the present invention include a range of glycosylation variants from a completely unglycosylated molecule to a modified glycosylated molecule. Altered glycosylation patterns may result from expression of recombinant molecules in different host cells.

Another aspect of the present invention extends to the variant HBV surface antigen molecule or its recombinant, derivative or chemical form or a variant HBV comprising said HBV surface antigen in composition form. Such compositions are particularly useful as therapeutic compositions and may be referred to herein interchangeably as biological, vaccine or pharmaceutical compositions. The biological compositions are particularly useful in inducing immunological memory against infection by an HBV variant such as an HBV escape mutant controlling by administering a variant HBV surface antigen or a recombinant, derivative or chemical form thereof or an HBV comprising same capable of inducing an immune response including immunological memory agents.

Accordingly, the present invention contemplates a composition comprising a variant HBV or an HBV surface antigen from said variant HBV or a recombinant or derivative form thereof or its chemical equivalent. The composition may be considered as a biological composition.

Generally, if an HBV is used, it is first attenuated. The biological composition according to this aspect of the present invention generally further comprises one or more pharmaceutically acceptable carriers and/or diluents.

The biological composition may comprise an HBV surface antigen or like molecule from one HBV variant or the composition may be a cocktail of HBsAgs or like molecules from a range of HBV variants including the referenced HBV. Similar inclusions apply where the composition comprises an HBV.

The biological composition forms suitable for injectable use include sterile aqueous solutions (where water soluble) or sterile powders for the extemporaneous preparation of sterile injectable solutions. It must be stable under the conditions of manufacture and storage and must be preserved against the contaminating action of microorganisms such as bacteria and fungi. The carrier can be a solvent or diluent containing, for example, water, ethanol, polyol (for example, glycerol, propylene glycol and liquid polyethylene glycol, and the like), suitable mixtures thereof, and vegetable oils. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the HBsAg or like molecule or HBV variant or reference strain in the required amount in the appropriate solvent or diluent as followed by sterilization such as by filter sterilization. In the case of sterile powders for the preparation of sterile injectable solutions, the preferred methods of preparation are vacuum drying and the freeze-drying technique which yield a powder of the immunointeractive molecule plus any additional desired ingredient from previously sterile-filtered solution thereof. Routes of administration contemplated by the present invention including intravenous, intraperitoneal, intrathelial, subcutaneous and intracerebral.

The biological composition of the present invention may also be given in oral, bucal, nasal spray, inhalation, patch, drip or suppository form.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the immunointeractive molecule, use thereof in the therapeutic compositions is contemplated. Supplementary active ingredients can also be incorporated into the compositions.

The HBV surface antigen or like molecule or HBV variant or reference strain will be added in a concentration effective to induce an interact immune response against the same molecule or an HBV carrying the same or an immunologically similar molecule. For example, an effective amount of HBV surface antigen may range from about 10 mg to about 2000 ng, or 50 ng to about 1000 mg or 100 ng to about 500 mg or other suitable effective amount. It is sometimes more convenient to express dosage amounts in terms of body weight. Accordingly, the effective amounts may be from, for example, about 0.5 ng/kg body weight to about 500 mg/kg body weight or an amount therebetween.

The subject invention extends to kits for assays for variant HBV. Such kits may, for example, contain the reagents from PCR or other nucleic acid hybridisation technology or reagents for immunologically based detection techniques.

The present invention further contemplates a variant of an isolated DNA virus which replicates via an RNA intermediate wherein said variant comprises a nucleotide mutation in a gene encoding a DNA polymerase resulting in at least one amino acid addition, substitution and/or deletion to said DNA polymerase in the manufacture of a medicament for the treatment and/or prophylaxis of hepatitis.

In a related embodiment, there is provided a use of a variant of an isolated DNA virus which replicates via an RNA intermediate wherein said variant comprises a nucleotide mutation in a gene encoding a viral surface component resulting in at least one amino acid addition, substitution and/or deletion in said viral surface component in the manufacture of a medicament for the treatment and/or prophylaxis of hepatitis.

In a further related embodiment, there is provide a use of a variant of an isolated DNA virus which replicates via an RNA intermediate wherein said variant comprises a nucleotide mutation in an overlapping portion of at least two open reading frames resulting in an amino acid addition, substitution and/or deletion to translation products of said open reading frames in the manufacture of a medicament for the treatment and/or prophylaxis of hepatitis.

The present invention also provides for the use of the subject HBV variants to screen for anti-viral agents. These anti-viral agents inhibit the virus. The term Ainhibit≅ includes antagonizing or otherwise preventing infection, replication, assembly and/or release or any intermediate step. Preferred anti-viral agents include nucleoside analogues, however, the present invention extends to non-nucleoside molecules.

Accordingly, another aspect of the present invention contemplates the use of a variant of an isolated DNA virus which replicates via an RNA intermediate wherein said variant comprises a nucleotide mutation in a gene encoding a DNA polymerase resulting in at least one amino acid addition, substitution and/or deletion to said DNA polymerase in in screening for an anti-viral agent capable of inhibiting said virus.

Another aspect of the present invention provides for the use of a variant of an isolated DNA virus which replicates via an RNA intermediate wherein said variant comprises a nucleotide mutation in a gene encoding a viral surface component resulting in at least one amino acid addition, substitution and/or deletion in said viral surface component in in screening for an anti-viral agent capable of inhibiting said virus.

Yet another aspect of the present invention is directed to the use of a variant of an isolated DNA virus which replicates via an RNA intermediate wherein said variant comprises a nucleotide mutation in an overlapping portion of at least two open reading frames resulting in an amino acid addition, substitution and/or deletion to translation products of said open reading frames in in screening for an anti-viral agent capable of inhibiting said virus.

The present invention is further described by the following non-limiting Examples.

EXAMPLES

In order to identify what other mutations may be selected during FCV therapy in the OLT setting, the inventors sequenced and analysed the HBV DNA polymerase encompassing the catalytic domains from 26 patients with high levels of HBV (greater than 90 pg/ml HBV DNA) undergoing FCV therapy and 10 patients with low levels of HBV (less than 90 pg/ml HBV DNA). Multiple serial samples were analysed, including prior to therapy and pre-OLT, during the FCV response phase post-OLT, and during HBV recurrence post OLT. The methods and results are shown in Examples 1 to 7.

Example 1

Patients and Methods

Treatment Protocol

The clinical details of the FCV prophylaxis liver transplantation protocol as previously described (19). Briefly, the aim of the study was to compare the safety and efficacy of oral FCV and IV penciclovir in reducing the risk of hepatitis B re-infection post-OLT in liver transplant patients. The study design was a multicentre, randomized, part double-blind, part placebo controlled trial in patients with end stage liver disease requiring OLT. Patients with HBV DNA levels more than 90 pg/ml at study entry (by hybridization) [high replicators] were treated with both FCV and HBIG post-OLT. These high replicators were treated with FCV (500 mg tds) to reduce HBV DNA levels prior to OLT. Famciclovir treatment was continued for 12 months post-OLT. An untreated control group of patients with HBV DNA levels less than 90 pg/ml [low replicators] at study entry were treated with HBIG alone post-OLT. In the original study, thirty six patients underwent OLT, and of these the clinical and virological outcome of twenty-two of the FCV treated patients has recently been presented (17 Manns). Essentially, FCV treated high replicators who became HBV DNA undetectable prior to OLT had HBV recurrences with similar frequency as low replicators treated with HBIG alone.

Example 2

Patients

Twenty six patients who had HBV levels more than 90 pg/ml at study entry (high HBV replicator [HR]) were treated with FCV pre-OLT and those patients who responded were then treated with HBIG plus FCV post-OLT. Of the 19 patients who responded to FCV and subsequently went to OLT, 9 did not have HBV recurrence 0-12 months post-OLT and 10 had HBV recurrence by 12 months post-OLT. Of the initial 26 patients, 6 did not initially respond to FCV and 1 was withdrawn from the study because of treatment with lamivudine. Ten patients who had HBV levels of less than 90 pg/ml at study entry (low HBV replicator [LR]) were treated only with HBIG post-OLT. Six of these patients had no HBV recurrence at 12 months post-OLT and 4 patients had HBV recurrence during the 12 months post-OLT.

Example 3

Extraction of HBV DNA from Patient Serum

HBV DNA was extracted from a total of 90 samples from 36 patients. Aliquots of 50 ml of sera were mixed with 150 ml TE (10 mmol/L Tris-HCl (pH 7.5), 2 mmol/L EDTA), 1% w/v sodium dodecyl sulfate and 1 mg/ml proteinase K, and incubated at 55° C. for 30 mins. DNA was deproteinized by phenol/chloroform extraction, precipitated with isopropanol and dissolved in 40 ml nuclease-free water.

Example 4

PCR Amplification

Two oligonucleotide primers (Bresatec, Adelaide, Australia) were used to amplify a fragment encompassing the catalytic domain of the polymerase protein and the Aa≅ determinant of the surface protein. The first round sense primer (5'-GCC TCA TTT TGT GGG TCA CCA TA-3' SEQ ID NO:1), and the antisense primer (5'-TCT CTG ACA TAC TTT CCA AT-3' SEQ ID NO:2) were used in the amplification. Each reaction was carried out using 5 ml of the extracted DNA as template, 1.5 U of Taq polymerase (Qiagen, Melbourne Australia), 1 mmol/L of sense and antisense primers, 200 mmol/L each of deoxynucleoside triphosphates, 50 mmol/L KCl, 3.5 mmol/L MgCl, 10 mmol/L Tris-HCl (pH 8.3) and 0.01% w/v gelatin. PCR was performed by 40 cycles of denaturation (94° C. for 45 sec), annealing (55° C. for 45 sec) and extension (72° C. for 1.5 min), followed by a final extension of 7 min (Perkin-Elmer 2400, Cetus, Norwalk, Conn.). If required, a further hemi-nested round of amplification was performed using 2 ml of first round product as template and primer 5' TTG GGG TGG AGC CCT CAG GTC 3' SEQ ID NO:3 as the sense primer. The amplification conditions were the same as the initial round except with only 25 rounds of cycling.

Example 5

Sequencing of the Polymerase/Envelope Genes of HBV DNA

Amplified products were gel purified using Geneclean II (BIO 101 Inc., La Jolla, Calif.) and were directly sequenced using the ABI Prism Big Dye Terminator Cycle Sequencing Ready Reaction Kit according to the manufacturers specifications (Perkin Elmer, Cetus Norwalk, Conn.). Electrophoresis was carried out by the Australian Genome Research Facility (Walter and Eliza Hall Institute, Melbourne). The PCR primers were used as sequencing primers as well as several additional primers (5'-AAA TTC GCA GTC CCC AAC-3' SEQ ID NO:4,5'-GAA AAT TGG TAA CAG CGG-3' SEQ ID NO:5, and 5'-GTA TCC CTC CTG TTG CTG T-3' SEQ ID NO:6) required to sequence the internal regions of the PCR products. MacVector and AssemblyLIGN (MacVector version 6.0 and AssemblyLIGN, Oxford Molecular, UK) was used to analyze all automatic sequence data. The deduced amino acid sequences were compared using the subprogram ClustalW.

Example 6

Sequence Analysis

Sequences were analyzed by comparison of the deduced amino acid sequence within the polymerase gene to the published polymerase consensus sequence (FIG. 2; Formula I; ref 18). A unique amino acid change was defined as a change to an amino acid which is not present in the HBV polymerase consensus sequence. Unique changes in the HBV isolates were compared to the individual pretreatment isolate and where appropriate, sequences were compared to other pretreatment samples. Any changes within the conserved polymerase domains A to E were noted (where domain A includes amino acids 421-436, Domain B includes 505-529, Domain C includes 546-555, Domain D includes 576-586 and Domain E includes 592-601). Due to the overlapping open reading frames for the genes encoding the polymerase and envelope (HBsAg), unique changes in the polymerase gene which alter the HBsAg were noted.

The deduced amino acid sequences for the surface antigen in the overlapping reading frame were compared to the 88 published sequences, genotypes A to F from Norder et al (20). An unique amino acid change was defined as a change which is not present in the published sequences (20). In addition, unique changes were compared to published amino acid changes detected after HBIG treatment and/or vaccination (21, 22, 23, 24, 25, 26). Due to the overlapping open reading frames for the polymerase and envelope genes, unique changes in the envelope gene which alter the polymerase were noted.

Example 7

Results

Outcome Analysis

In this study, famciclovir (FCV) was given prophylactically pre-OLT to patients with end-stage liver failure due to chronic HBV infection with serum HBV DNA levels greater than 90 pg/ml, [high replicators (HR)]. The patients were then subsequently treated with HBIG and FCV post-OLT. Samples were taken for sequencing pretreatment with FCV, pre-OLT, during the FCV responding phase post-OLT and then in those cases with rising viraemia during HBV recurrence. HBV DNA sequence was examined from 36 patients. These patients included 26 high replicators [HBV DNA greater than 90 pg/ml at study entry (HR)] who were treated with both FCV and HBIG. Of these patients, 19 responded pre-OLT, 6 did not initially respond and 1 patient was withdrawn because of treatment with lamivudine. The 19 patients who responded underwent OLT and 9 of these patients had no HBV recurrence at 12 months post-OLT and sera were available post-OLT for 7 of these patients. The remaining 10 of these patients had HBV recurrence. Serum samples were available for study from seven of these patients after HBV recurrence post-OLT. The 10 patients treated with HBIG alone had pre-OLT serum HBV DNA levels of less than 90 pg/ml [low replicators (LR)]. Of these, 4 patients had HBV recurrence in the 12 months post-OLT. Sera was available from three of these patients pre-OLT and from two patients after HBV recurrence. Six patients had no HBV recurrence at 12 months post-OLT and sera was available from five of these patients post-OLT.

Sequence Analysis (A) Patients with HBV DNA Greater than 90 pg/ml (HR Group)

Pre OLT Phase (i) FCV Responders

Nineteen of the original 26 HR patients responded to FCV. (One further patient responded but was withdrawn from further analysis because of subsequent treatment with lamivudine.) There were 28 unique amino acid changes throughout the region encompassing the catalytic region of the polymerase when compared to the published sequences (Table 2). This includes 9 unique mutations within the functional domains in 8 patients who responded to FCV. These were at L423F (A domain), I508V (B domain), V/L/M553I/M (C domain), N/Q584S (D domain), N/Q584H (D domain), S592H (E domain), N594H (E domain), N594H/Y (E domain), and M596T/M (E domain).

There were also 28 unique changes in the HBsAg in these pretreatment isolates compared to the sequences published in Norder et al., (20) [Table 2]. Of these mutations, 8 amino acids have been previously noted either at the same position or are the identical amino acid reported associated with either vaccine escape or selection after HBIG treatment post OLT. Three of these were at amino acid position 120 (P/S/A120S/A/T/P, P/S/A120T and P/S/A120T/P) and four were at amino acid position 134 (F/Y/I134V, F/Y/I134N/Y, F/Y/I134S and F/Y/I134N). The other change was at D/A144E/N.

(ii) FCV Non-Responders

Six patients with high levels of HBV DNA [HR] pre-transplantation did not respond to FCV treatment. There were 10 unique amino acid changes from HBV isolated from all six patients when compared to the previously published polymerase consensus (Table 4). Of these, there were 4 amino acids H436N/H, S463S/Y, V537V/I and K587R which were not present in the 19 FCV responders (Table 1). The changes detected in the polymerase gene at position 463, 537, 560, and 565 (in 2 isolates) all resulted in an altered HBsAg in the overlapping reading frame (Table 4).

There were 8 unique amino acid differences in the HBsAg compared to the sequences in Norder et al (20) in 5/6 patients. These include the 5 changes noted above which also resulted in a unique mutation in the polymerase gene, P/S/A 120Y/S and S204R, which resulted in a change in the polymerase gene that appears in the polymerase consensus sequence (ie.

not unique) and P217L, which did not result in a change to the polymerase gene. One of these amino acids is located at the same position as a known HBIG selected variant (P120Q) at P/S/A120Y/S.

Post OLT Phase (i) HBV Recurrence

Ten of the nineteen patients with high levels of HBV DNA at study entry [HR] had recurrence post-OLT within the first 12 months. Of these patients, sera were available after recurrence for sequence analysis from 7 patients. There were 15 unique changes in 5/7 patients compared to the previously published consensus sequence, or in the individual pretreatment sequences from these patients, including 10 within the conserved domains (Table 5). Eight of these 15 unique amino acid differences (detected in 4/7 patients) were also not detected in any pretreatment samples from the 19 patients who responded to FCV pre OLT, nor in the post-OLT samples from the 9 patients treated with FCV without recurrence. These were L423L/M/V (A domain), H436H/Y (A domain), H436Y (A domain), a deletion of amino acids 471-474, W499E, V519L (B domain), N584N/K (D domain) and R588R/K (Table 5). The change at V519L is the same as previously reported after long term FCV therapy (27). The L526M mutation which has been previously reported after long term FCV therapy (27), was also detected in this study in one sample from a patient who responded to FCV (Table 5) but was not detected in latter samples from the same patient. The H436Y mutation was seen in isolates from two different patients with recurrence, and in both cases was seen as a transitory change (i.e. had reverted to the original sequence in the next sample). A change at this amino acid position to a different residue was also seen in a non-responder (see above).

The 15 unique changes in the HBV polymerase were then examined to determine if there was any alteration in the HBsAg in the overlapping reading frame (Table 5). The deletion at residues 471-474 was found to result in a corresponding in-frame deletion in the envelope gene (aa 117-120). The H436Y, H436H/Y, S483T, I508V and L526M mutations did not result in any change to the envelope gene sequence. The L423L/M/V altered the HBsAg sequence to I68I/M, the mutation at L423F/L altered the HBsAg to C69F/L, the V519L resulted in E164D in the HBsAg sequence and S565A altered the HBsAg at S210R. The mutation at W499E (due to 2 nucleotide changes) resulted in a change at both D144E and G145R in the HBsAg sequence (a known vaccine escape mutant) and the N584N/K, N584S, R588R/K and the N594H changes were located after the end of the HBsAg gene. The HBsAg termination codon at position 226 overlaps with the codon encoding amino acid 582 in the polymerase gene.

There were a total of 11 unique amino acid changes in HBsAg when compared to the published sequences of Norder et al., (20) and the individual pretreatment sequences. This includes the seven mutations listed above which changed the HBV polymerase and P67P/Q, P67Q, R73P and M133T which did not alter the HBV polymerase. Of these 11 changes, two in one patient have been previously reported as vaccine or HBIG escape (D144E and G145R). The 5 unique changes in the HBsAg post-OLT in patients with HBV recurrence not detected in any pretreatment sample are listed in Table 6.

(ii) HBV Non-Recurrence

Nine of the HR patients treated with FCV and HBIG did not have HBV recurrence in the 12 months following OLT and sera was available from 7 patients for sequence analysis. There were 12 unique changes in three patients compared to the previously published HBV polymerase consensus sequence that were not present in the individual's pretreatment sample. These included 5 changes in the functional domains and were at L423L/F (A domain), A432V (A domain), R466K, N477T, N485N/K, G498E, L526M (B domain), T530S, N572K, F573Y, L577L/M/V (D domain) and L593G/V/L/STOP (E domain). The L526M mutation was detected only during a peak of HBV DNA immediately after transplantation and was not detected in subsequent isolates from this patient. Nine of the 12 unique polymerase mutations resulted in an altered HBsAg in the overlapping reading frame as shown in parentheses, L423L/F (C69C/F/S/Y), A432V (R78L), R466K (G112R), N477T (T123P), N485N/K (N131N/I/T/S), G498E (D144N), T530S (L176V), N572K (I218N) and F573Y (F219I).

There were 11 unique changes in the HBsAg post treatment when compared to the sequences listed by Norder et al. (20) and the individual's pretreatment isolate. These were C69C/S/F/Y, R78L, T123P, T131N/I/T/S, D144N, C147S/Y, S167L, L173R, L176V, I218N and F219I. The changes at C147S/Y, S167L and L173R did not result in a change in the overlapping polymerase reading frame, whereas the other unique HBsAg mutations all resulted in a change in the polymerase (listed above). The T131N/I/T/S mutation has previously been detected after HBIG treatment and the changes at T123P and D144N are at the same position as other previously reported HBIG associated changes. These patients did not have HBV recurrence even in the presence of these previously noted HBIG associated variants. No amino acid sequence in this patient group was noted that was common to all non-recurrence patients which was not present in HBV isolates from patients with recurrence nor FCV nonresponder.

(B) Patients with HBV DNA Less than 90 pg/ml (HR Group).

Pre-OLT Phase

Multiple HBV isolates from transplant patients treated with HBIG only and not FCV were sequenced to determine the background sequence variation over a comparable time interval in the transplantation setting.

Of the 10 patients with low levels of viremia, serum samples were available from 9 patients pre-OLT. Sequencing of these isolates demonstrated that there were 12 unique changes isolated from five patients compared to the published HBV polymerase consensus sequence. These were at S/D455P, N469D, Y494F, Y/F497L, S/F565A/S, F/V573F/L, P583T (D Domain), N/Q584S (D domain), K585K/G (D Domain), S592N (E domain), L593L/I/V (E domain) and N594H (E domain).

In the HBsAg of these pretreatment isolates, five amino acid variants were detected in 4 patients when compared to the sequences published by Norder et al. (20). These variants were at P/S/A120Q P/S/A120T, S/N210A/S, S/N210R/S and F219Y/F. The first two of these HBsAg changes have been previously associated with HBIG selected changes post OLT (23).

Post-OLT Phase (i) HBV Recurrence

Serum samples suitable for sequencing were available from only two patients who had HBV recurrence during HBIG treatment. The HBV sequence characterized from these two patients revealed that there were 6 unique changes compared to the published consensus and the individual's pretreatment sample. These were N469D, L492S, Y494F, T496T/N, Y497L and S548S/R(C domain). The L492S, the T496T/N and the S548S/R also changed the HBsAg at C138R, T142T/P and A194G/A, respectively. The other changes did not alter the HBsAg. Domain A is the only conserved domain region in which there were no unique changes selected in HBV isolates from LR patients post OLT whereas several changes were selected in this domain during FCV treatment in HR HBV isolates (see Section A above).

Within the HBsAg there were 6 unique changes in two patients when compared to the published sequences (20) and the individual=s pretreatment sample. These were V96A, P120Q, C138R, P142T/P, K160K/N and A194G/A. The K160K/N mutation resulted in a change of the HBV polymerase at I515I/L. The other changes which affected both overlapping reading frames are listed above. Five of these changes were not detected in any pretreatment sample (Table 5). The mutation at P120Q was detected pretreatment, and has previously been reported to be selected after HBIG treatment (23).

(ii) HBV Non-Recurrence

Sera was available from five out of the six patients post-OLT without HBV recurrence. In two of these patients there were 5 changes in the polymerase gene compared to the published consensus and the individual's pretreatment isolate. These were at L/S/R563R/C, L581L/F (D domain), L581L/Stop (D domain) and P583P/R (D domain) and L593L/I (E Domain). Only the L/S/R563R/C mutation altered the HBsAg in the overlapping reading frame at I208I/M.

The I208I/M was the only unique change detected in the HBsAg sequences compared to those listed by Norder et al (20) and the individual=s pretreatment sample. This change has not been previously noted with vaccine or HBIG escape. The amino acid variant (P/S/A120T, a known HBIG selected variant) was detected in one patient's pretreatment isolate. This was not detected in this patients post treatment isolates and the patient did not have recurrence.

TABLE 2

Unique HBV polymerase changes in the pretreatment isolates from FCV responders

| Amino acid differences compared to the published HBV polymerase consensus sequence | Corresponding HBsAg change |
|---|---|
| L423F | C69S |
| S452A | no change |
| S/D455P | no change |
| L461V | no change |
| S462A | C107W |
| Q471L | S117C |
| H/Y 472R | no change |
| H479H/Q | T/M125M/T/K/R |
| S483T | no change |
| V488E | F/Y/I134S |
| V488E/V | F/Y/I/134N/Y |
| V488G | F/Y/I134V, M/K/L133T |
| R/W499G/W | D/A144G |
| I508V | no change |
| I533L | no change |
| V/L/M533I/M | After stop codon |
| V/G560E | Y/F/H/C206N |
| V/G560P | K/N/S204R |
| Q/E561S | S/G/H/N/D/T207R |
| Q/E561 Q/Stop | no change |
| S/F565A | S/N210R |
| T/A568S | I/L/M213F |
| N/Q584S | After HBsAG Stop |
| N/Q584H | After HBsAG Stop |
| S592H | After HBsAG Stop |
| N594H | After HBsAG Stop |
| N594H/Y | After HBsAG Stop |
| M596T/M | After HBsAG Stop |

TABLE 3

Unique HBV HBsAg changes in the pretreatment isolates from FCV responders

| Amino acid differences compared to the published HBV HBsAg sequences | Corresponding HBV polymerase change |
|---|---|
| P67Q | no change |
| C69S | L423F |
| R73P | no change |
| R79H | no change |
| L94STOP | no change |
| V96A | no change |
| Q101R | no change |
| C107W | S462A |
| S117C | Q417L |
| P/S/A120S/A/T/P | T/P/N/I474I/T/N/S |
| P/S/A120T | no change |
| P/S/A120T/P | no change |
| T/M125M/T/K/R | H479Q |
| M/K/L133T | V488G |
| F/Y/I134N/Y | V488V/E |
| F/V/I134V | V488G |
| F/Y/I134S | V488E |
| F/Y/I134N | V488E |
| S/T143M | no change |
| D/A144E/N | R/W499G/W |
| A/G166V | no change |
| K/N/S204R | no change |
| Y/F/H206N | V/G560E |
| S/G/H/N/D/T207R | Q/E561S |
| S/N210R | S/F565A |
| I/M/L213F | T/A568S |
| P214L | no change |
| P217L | no change |

TABLE 4

Summary of amino acid changes in HBV variants isolated from FCV non-responders compared to the published consensus sequence (18)

| Amino acid differences compared to the published HBV polymerase consensus sequence | Corresponding HbsAg change | Amino acid change in other patient groups |
|---|---|---|
| **H436N/H** | no change | H436H/Y (3-6[a], 27-3[a]) |
| **S463S/Y** | L109I/L | not detected |
| **V537V/I** | C/W182Y/Stop | not detected |
| V/G560E | Y206N | V560E (15-1[b]) |
| S/F565A/S<br>S/F 565 A | S210R/S | S/F 565A (4-1[b], 10-1[b], 18-1[b]) |
| N/Q584H | After end HbsAg | N/Q584H (15-1[b])<br>N/Q584 S (2-3[a], 3-1[b], 26-1[c])<br>N/S/H 584N/K (3-3[a]) |
| **K587R** | After end HBsAg | not detected |
| N594H | After end HbsAg | N594H (2-3[a], 14-1[b], 15-1[b], 17-1[b], 26-1[c], 31-1[c])<br>N594N/Y (2-1[b]) |

Amino acid changes in bold were not detected in patients who responded to FCV

[a]= HBV isolated from patients with HBV recurrence during FCV treatment

[b]= HBV isolated from a pretreatment isolate from a FCV treated responder

[c]= HBV isolated from a pretreatment isolate from an HBV low replicator not treated with FCV

TABLE 5

Summary of amino acid differences in HBV variants isolated during HBV recurrence from FCV treated patients compared to the publsihed consensus

| Amino acid differences compared to the published HBV polymerase consensus sequence | Corresponding HbsAg change | Amino acid change in other patient groups |
|---|---|---|
| L423L/M/V | I68I/M | L423F/L (15-2[a])<br>L423F (12-1[e]) |
| L423L/F | C69F/L | L423F/L (15-2[a])<br>L423F (12-1[e]) |
| H436H/Y<br>H436Y | no change | H436N (32-2[b]) |
| DEL 471-474 | 117-120 | not detected |
| S483T | no change | S483T (2-1[e]) |
| W499E | D144E/G145R | R499K (1-2[c]) |
| I508V | no change | I508V (2-1[e]) |
| V519L | E164D | V519L (1-3[c]) |
| L526M | no change | L526M (1-3[c], 6-2[a,g]) |
| S565A | S210R | S565A (4-1[e], 10-1[e], 18-1[e]) |
| N584S | after HBsAg stop | N/Q584S (3-1[e], 26-1[c])<br>N584H (15-1[f], 32-1[b]) |
| N/S/H584N/K | after HBsAg stop | N/Q584S (3-1[e], 26-1[c])<br>N584H (15-1[f], 32-1[b]) |
| R588R/K | after HBsAg stop | not detected |
| N594H | after HBsAg stop | N594H (14-1[e], 15-1[e], 17-1[e], 24-1[b], 25-1[b], 26-1[f], 31-1[e])<br>N594N/Y (2-1[e]) |

Amino acid changes in bold were not detected in patients who responded to FCV, nor in patients with HR HBV who did not have HBV recurrence post-OLT.

[a]HR FCV Responder pre-OLT, non-recurrence post OLT

[b]HR non-responder

[c]LR with recurrence post OLT, treated with FCV post recurrence

[d]HR non-recurrence

[e]HR FCV responder pre-OLT

[f]LR pre-OLT

[g]Transitory change

TABLE 6

Unique changes in HBsAg in patients with HBV recurrence comparison to Norder et al. (20) and all HBsAg pretreatment sequences

| HBsAg change | Isolate | FCV treatment | HBV polymerase equivalent |
|---|---|---|---|
| I68I/M | 5-2 | FCV + HBIG | L423L/M/V |
| DEL 117-120 | 4-3 | FCV + HBIG | DEL 471-474 |
| D144E | 4-3 | FCV + HBIG | W499E |
| G145R | 4-3 | FCV + HBIG | W499E |
| E164D | 27-3, 4, 5 | FCV + HBIG | V/G519L |
| V96A | 26-3 | HBIG | no change |
| C138R | 26-3 | HBIG | L492S |
| P142T/P | 28-4 | HBIG | T496T/N |
| K160K/N | 26-4 | HBIG | I515I/L |
| A194G/A | 26-3 | HBIG | S/A548S/R |

BIBLIOGRAPHY

1. Summers J, Mason W. *Cell* (1982) 29: 403-415.
2. Vere Hodge R. A. *Antiviral Chem Chemother* (1993) 4:67-84.
3. Boyd M R et al *Antiviral Chem Chemother*. (1987) 32: 358-363.
4. Kruger T et al *Hepatology* (1994) 22: 219A.
5. Main J et al. *J. Viral Hepatitis* (1996) 3:211-215.
6. Severini A et al *Antimicrobial Agents Chemother* (1995) 39: 1430-1435.
7. Dienstag J L et al *New England J Med* (1995) 333: 1657-1661.
8. Shaw T, et al. *Antimicrobiol Agents Chemother* (1994) 38:719-723.
9. Shaw T, et al. *Hepatology* (1996) 24: in press.
10. Tsiquaye K N, et al. *J. Med Virol* (1994) 42: 306-310.
11. Boker K H W, et al. *Transplantation* (1994) 57: 1706-1708.
12. Angus P, et al. *J. Gastroenterol Hepatol* (1993) 8: 353-357.
13. Poch O. et al. *EMBO J.* (198.9) 8: 3867-3874.
14. Delarue M, et al. *Protein Engineering* (1990) 3: 461-467.
15. Chiou H C, et al. *Antiviral Chem Chemother* (1995) 6: 281-288.
16. Ling R, et al. *Hepatology* (1996) 24: 711-713.
17. Price P M, et al. *Hepatology* 1992 16: 8-13.
18. Bartholomeusz et al., Intervirology 1997
19. Manns M, et al, *Hepatology* 1998 28 (4 part 2) 260A.
20. Norder H, et al., *J Gen Virol* 1993 74: 1341-1348.
21. Wallace L A and Carman W F, *Viral Hepatitis Reviews* 1997 3: 5-16.
22. Protzer-Knolle U et al, *Hepatology* 1998 27: 254-263.
23. Carman W F, Thomas H C. *Gastroenterology* 1992 102: 711-719.
24. Moriyama K, et al. *Lancet* 1991 337: 125.
25. Ghany M G et al, *Hepatology* 1998 27: 213-222.
26. Cariani E, et al, *Journal of Medical Virology* 1995 47: 410-415.
27. Aye T T, et al., *Journal of Hepatology* 1997 26:1148-1153.
28. Xiong, et al., *Hepatology* 1998 28 1669-1673
29. Allen M I, et al., *Hepatology* 1998 27: 1670-1677.
30. Niesters H G M, et al., *Journal of Infectious Diseases* 1998 177:1382-5.
31. Chayama K, et al., *Hepatology* 1998 1711-1716.
32. Ladner S K, et al., *Antiviral Chemistry & Chemotherapy* 1998 9: 65-72.
33. Tipples G A, et al., *Hepatology* 1996 24:714-717.
35. Bartholomew M M, et al., *Lancet* 1997 349:20-22.
36. Cane P A, et al., Submitted 1998.
37. Wolters L M M, et al., *Journal of Hepatology* 1998 28: 909-911.
38. Naoumov N V, et al., *Hepatology* 1996 24:282A
39. Zoulim F, et al., *Hepatology* 1997; Abstr. 1200.
40. Xiong X, et al., 11th International Conference on Antiviral Research, San Diego, April 1998.
41. Melegari M, et al., *Hepatology* 1998 2:628-633.
42. Ono-Nita S K, et al., Antiviral Therapy 1997; Abstr. 017. Second International Conference on Therapies for Viral Hepatitis. Hawaii.
43. Batholomeusz A I, et al., Antiviral Therapy 1997; Abstr. P72. Second International Conference on Therapies for Viral Hepatitis. Hawaii
44. Tillman H L, et al., *Hepatology* 1997 26: 4. Abstr. 1202.
45. Fu L, et al., *Biochemical Pharmacology* 1998 55:1567-1572.
46. Pillay D, et al., *International Antiviral News* 1998.

We claim:

1. A method for determining the potential for an HBV to exhibit reduced sensitivity to a nucleoside analogue, said method comprising isolating DNA or corresponding mRNA from said HBV and screening for one or more mutation(s) in the nucleotide sequence encoding HBV DNA polymerase resulting in at least one amino acid substitution in the D domain of said DNA polymerase wherein the presence of such a mutation is an indication of the likelihood of resistance to said nucleoside analogue, wherein said one or more mutation(s) is selected from the group consisting of N584S, N584K, S/H584N/K, R588K, N/Q 584H, K587R in the following sequence:

$Z_{47}Z_{48}$GIHLNP$Z_{49}$KTKR (SEQ ID NO:9)

wherein $Z_{47}$ is S or D; $Z_{48}$ is L or V, and $Z_{49}$ is N or Q, wherein the notation defines a codon number position of HBV genotype with reference to codon 550 being methionine in the YMDD motif, the letter(s) proceeding the number in the notation of the mutation being at least one wild-type or permutation amino acid at said codon number position, and the letter(s) subsequent to the number in the notation being at least one post-mutation amino acid at said codon number position, wherein $Z_{47}$ is codon number position 576 of the HBV genotype.

* * * * *